US010939051B2

(12) United States Patent
Nakamura et al.

(10) Patent No.: US 10,939,051 B2
(45) Date of Patent: Mar. 2, 2021

(54) IMAGE PROCESSING APPARATUS AND IMAGE PROCESSING METHOD, AND ENDOSCOPIC SYSTEM

(71) Applicant: SONY CORPORATION, Tokyo (JP)

(72) Inventors: Yukihiro Nakamura, Kanagawa (JP); Takeshi Miyai, Kanagawa (JP); Tomoyuki Hirayama, Kanagawa (JP); Masaya Takemoto, Kanagawa (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 16/486,935

(22) PCT Filed: Feb. 19, 2018

(86) PCT No.: PCT/JP2018/005653
§ 371 (c)(1),
(2) Date: Aug. 19, 2019

(87) PCT Pub. No.: WO2018/159346
PCT Pub. Date: Sep. 7, 2018

(65) Prior Publication Data
US 2020/0236271 A1 Jul. 23, 2020

(30) Foreign Application Priority Data

Mar. 3, 2017 (JP) .............................. JP2017-040137

(51) Int. Cl.
*A61B 1/045* (2006.01)
*H04N 5/235* (2006.01)
(Continued)

(52) U.S. Cl.
CPC ....... *H04N 5/2354* (2013.01); *A61B 1/00009* (2013.01); *G06T 5/002* (2013.01);
(Continued)

(58) Field of Classification Search
CPC ..... G09G 2320/0233; G09G 2320/062; G09G 2320/0673; H04B 10/54;
(Continued)

(56) References Cited

U.S. PATENT DOCUMENTS 5,920,646 A * 7/1999 Kamon ................ H04N 1/4092
382/173
2006/0066642 A1 * 3/2006 Ookawara ................ G09G 3/20
345/690
(Continued)

FOREIGN PATENT DOCUMENTS

CN 104379050 A 2/2015
EP 2353537 A1 8/2011
(Continued)

OTHER PUBLICATIONS

International Search Report and Written Opinion of PCT Application No. PCT/JP2018/005653, dated May 15, 2018, 08 pages of ISRWO.

*Primary Examiner* — Daniel Chang
(74) *Attorney, Agent, or Firm* — Chip Law Group

(57) ABSTRACT

The present technology relates to an image processing apparatus and method and an endoscopic system that permit reduction of uneven illumination distribution. An image processing apparatus includes a signal processing section that corrects uneven illumination of an image shot with a subject within a body of a patient to be operated on illuminated by a light source. The light source is arranged within the patient's body. The signal processing section corrects uneven illumination on the basis of a normally illuminated image and a low illuminated image. The normally illuminated image is shot with the subject within the body illuminated at a given illumination intensity. The low illuminated image is shot with the subject illuminated at a lower illumination intensity than the given illumination intensity.

10 Claims, 13 Drawing Sheets

(51) Int. Cl.
  *A61B 1/00*    (2006.01)
  *G06T 5/00*    (2006.01)
  *H04N 5/225*   (2006.01)
  *H04N 7/18*    (2006.01)

(52) U.S. Cl.
  CPC ......... *H04N 5/2256* (2013.01); *H04N 5/2351* (2013.01); *H04N 7/183* (2013.01); *H04N 2005/2255* (2013.01)

(58) Field of Classification Search
  CPC ........ G06T 2207/10152; H04N 1/6027; H04N 9/3182; H04N 5/2351
  USPC ................... 345/63, 77, 690; 382/274, 169; 358/509; 348/362; 250/372
  See application file for complete search history.

(56) References Cited

U.S. PATENT DOCUMENTS

| | | |
|---|---|---|
| 2007/0027362 A1 | 2/2007 | Handa et al. |
| 2010/0171774 A1* | 7/2010 | Mizukoshi ........... G09G 3/3275 345/690 |
| 2010/0214630 A1* | 8/2010 | Takaura ............. H04N 1/02815 358/474 |
| 2010/0225797 A1* | 9/2010 | Pertsel ................... H04N 5/243 348/311 |
| 2011/0257488 A1 | 10/2011 | Koyama et al. |
| 2014/0118558 A1* | 5/2014 | Imoto .................. G09G 3/3208 348/181 |
| 2015/0092035 A1 | 4/2015 | Yamamoto et al. |
| 2015/0230698 A1* | 8/2015 | Cline ..................... A61B 1/051 600/109 |

FOREIGN PATENT DOCUMENTS

| | | |
|---|---|---|
| EP | 2859837 A1 | 4/2015 |
| JP | 2007-075366 A | 3/2007 |
| JP | 2007-105218 A | 4/2007 |
| JP | 2007-260397 A | 10/2007 |
| JP | 2012-100733 A | 5/2012 |
| JP | 3176102 U | 6/2012 |
| JP | 2013-255655 A | 12/2013 |
| JP | 2016-049342 A | 4/2016 |
| WO | 2010/050244 A1 | 5/2010 |
| WO | 2013/187215 A1 | 12/2013 |

* cited by examiner

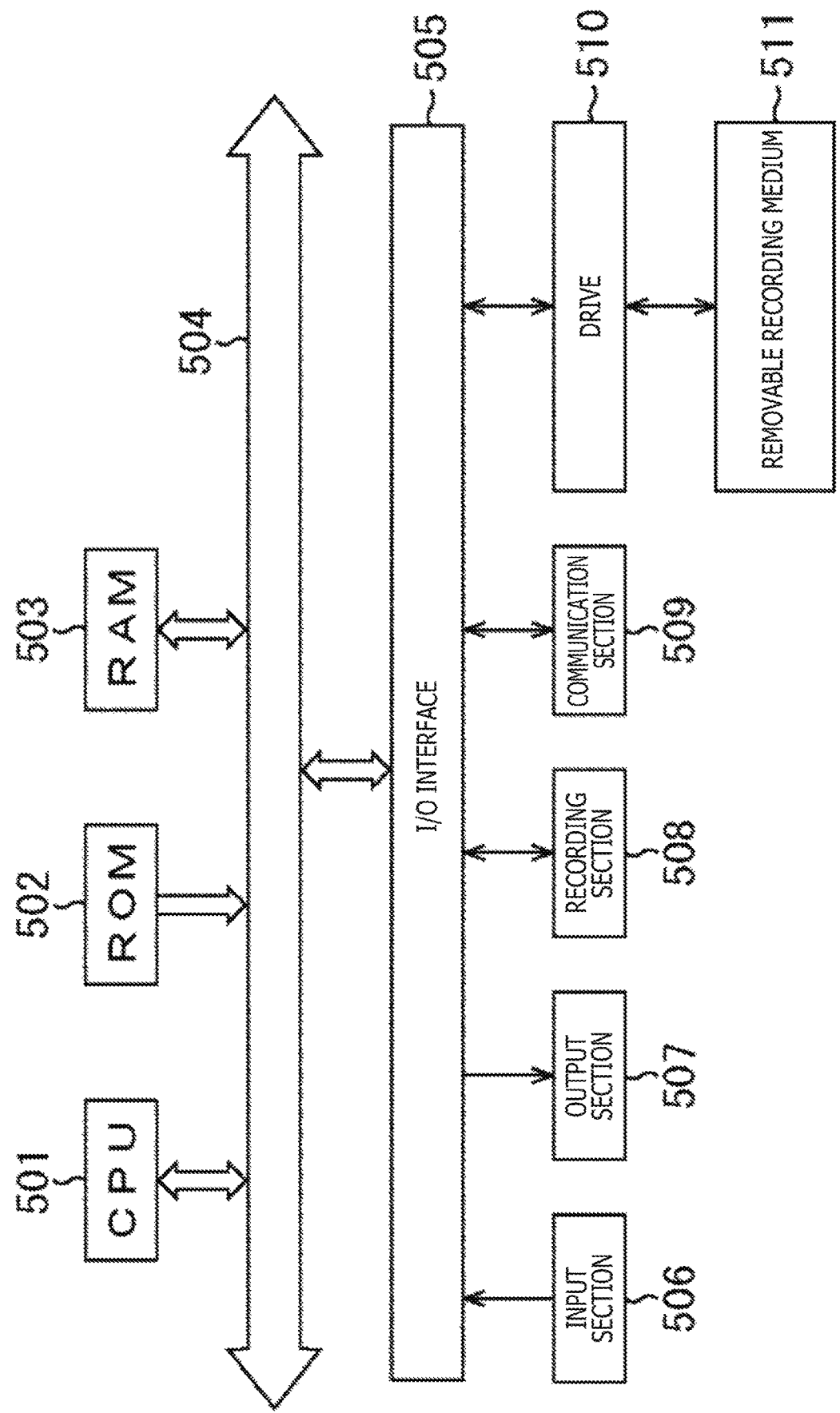

IMAGE PROCESSING APPARATUS AND IMAGE PROCESSING METHOD, AND ENDOSCOPIC SYSTEM

CROSS REFERENCE TO RELATED APPLICATIONS

This application is a U.S. National Phase of International Patent Application No. PCT/JP2018/005653 filed on Feb. 19, 2018, which claims priority benefit of Japanese Patent Application No. JP 2017-040137 filed in the Japan Patent Office on Mar. 3, 2017. Each of the above-referenced applications is hereby incorporated herein by reference in its entirety.

TECHNICAL FIELD

The present technology relates to an image processing apparatus and method and an endoscopic system, and in particular, to an image processing apparatus and method and an endoscopic system that permit reduction of uneven illumination distribution.

BACKGROUND ART

Against the backdrop of increasing demand for minimal invasiveness in medical care witnessed in recent years, minimization of incision wounds, wounds that may affect postoperative QoL (Quality of Life), has been sought after. For this reason, the reduction in diameter of a rigid endoscopic scope has been required in surgeries using a rigid endoscope.

Rigid endoscopes commonly used today include an optical transmission channel in the rigid endoscopic scope, with illuminating light shined from a tip of the rigid endoscopic scope. This results in an increased diameter of the rigid endoscopic scope by as much as the size of the optical transmission channel in the rigid endoscopic scope, thus hampering the reduction in diameter.

On the other hand, a technique has been proposed to insert, separately from the rigid endoscopic scope, a plurality of light sources into a patient's body, keep the light sources therein, and shine illuminating light over a wide area in a body cavity (refer, for example, to PTL 1).

CITATION LIST

Patent Literature

[PTL 1]
 Japanese Patent Laid-Open No. 2007-260397

SUMMARY

Technical Problem

However, in a case where light sources kept within the patient's body are used, uneven illumination distribution occurs due to non-uniform overlapping of illuminating light produced by the plurality of light sources.

Also, a positional relationship between the light sources and organs and other body parts within a field of view varies over time because of pulsation of the organs and blood vessels in the body, deformation of the organs and blood vessels within a surgical field caused by a surgery, and so on. This may lead to variation of uneven illumination distribution on an endoscopic image acquired over time.

In light of the foregoing, it is an object of the present technology to permit reduction of uneven illumination distribution.

Solution to Problem

An image processing apparatus of a first aspect of the present technology includes a signal processing section. The signal processing section corrects uneven illumination of an image shot with a subject within a body of a patient to be operated on illuminated by a light source. The light source is arranged within the patient's body. The signal processing section corrects uneven illumination on the basis of a normally illuminated image and a low illuminated image. The normally illuminated image is shot with the subject within the body illuminated at a given illumination intensity. The low illuminated image is shot with the subject illuminated at a lower illumination intensity than the given illumination intensity.

An image shot with illumination produced by the light source halted can be used as the low illuminated image.

A light source control section for controlling illumination produced by the light source can be further provided in the image processing apparatus.

The signal processing section can be caused to calculate a correction parameter for correcting the uneven illumination on the basis of the normally illuminated image and the low illuminated image and correct the uneven illumination of the image on the basis of the correction parameter.

The signal processing section can be caused to calculate the correction parameter on the basis of a rate of change in luminance between the normally illuminated image and the low illuminated image.

The signal processing section can be caused to calculate the correction parameter at a given position on the basis of the rate of change in luminance at the given position and the rate of change in luminance at a position different from the given position.

A shooting section can be further provided in the image processing apparatus. The shooting section includes a rigid endoscopic scope and shoots the image by receiving light incident from the subject within the body via the rigid endoscopic scope.

A video including each of the normally illuminated image and the low illuminated image as a frame can be used as the image.

The signal processing section can be caused to generate an output video by correcting the uneven illumination of the video and performing a noise reduction process on a video acquired by the uneven illumination correction.

In a case where the video frame is the low illuminated image, the signal processing section can be caused to generate a frame of the output video by correcting the uneven illumination of the low illuminated image first, followed by adjusting a gain and performing the noise reduction process on the image acquired by the gain adjustment. In a case where the video frame is the normally illuminated image, the signal processing section can be caused to generate a frame of the output video by correcting the uneven illumination of the normally illuminated image and performing the noise reduction process on the image acquired by the uneven illumination correction.

In a case where the video frame is the low illuminated image, the signal processing section can be caused to perform the noise reduction process on the image acquired by the gain adjustment at a higher processing intensity than in a case where the video frame is the normally illuminated image.

An image processing method of a first aspect of the present technology includes a step of correcting uneven illumination of an image shot with a subject within a body of a patient to be operated on illuminated by a light source. The light source is arranged within the patient's body. The uneven illumination is corrected on the basis of a normally illuminated image and a low illuminated image. The normally illuminated image is shot with the subject within the body illuminated at a given illumination intensity. The low illuminated image is shot with the subject illuminated at a lower illumination intensity than the given illumination intensity.

In the first aspect of the present technology, uneven illumination of an image is corrected. The image is shot with a subject within a body of a patient to be operated on illuminated by a light source. The light source is arranged within the patient's body. The uneven illumination is corrected on the basis of a normally illuminated image and a low illuminated image. The normally illuminated image is shot with the subject within the body illuminated at a given illumination intensity. The low illuminated image is shot with the subject illuminated at a lower illumination intensity than the given illumination intensity.

An endoscopic system of a second aspect of the present technology includes a shooting section and a signal processing section. The shooting section includes a rigid endoscopic scope and shoots an image by receiving light incident from a subject within a body of a patient to be operated on via the rigid endoscopic scope. The signal processing section corrects uneven illumination of the image shot by the shooting section with the subject within the patient's body illuminated by a light source arranged within the patient's body. The signal processing section corrects the uneven illumination on the basis of a normally illuminated image and a low illuminated image. The normally illuminated image is shot with the subject within the body illuminated at a given illumination intensity. The low illuminated image is shot with the subject illuminated at a lower illumination intensity than the given illumination intensity.

In the second aspect of the present technology, an image is shot by receiving light incident from a subject within a body of a patient to be operated on via a rigid endoscopic scope. Uneven illumination of the image shot by the shooting section is corrected. The image is shot with the subject within the patient's body illuminated by a light source arranged within the patient's body. The uneven illumination is corrected on the basis of a normally illuminated image and a low illuminated image. The normally illuminated image is shot with the subject within the body illuminated at a given illumination intensity. The low illuminated image is shot with the subject illuminated at a lower illumination intensity than the given illumination intensity.

Advantageous Effect of Invention

According to the first and second aspects of the present technology, it is possible to ensure reduced uneven illumination distribution.

It should be noted that the effect described here is not necessarily restrictive and may be any of the effects described in the present disclosure.

BRIEF DESCRIPTION OF DRAWINGS

FIG. 13 is a diagram illustrating a configuration example of a computer.

DESCRIPTION OF EMBODIMENTS

A description will be given below of embodiments to which the present technology is applied with reference to drawings.

First Embodiment

<Configuration Example of the Endoscopic System>

The present technology corrects uneven illumination by synchronizing an indwelling light source and a shooting section including a rigid endoscopic scope, acquiring an image under low illumination at a given time interval, and calculating a difference between the acquired image and an image adjacent in a time direction acquired under normal illumination. This eliminates the need for an optical transmission channel for illumination in the rigid endoscopic scope, thus realizing reduction in diameter of the rigid endoscopic scope, ensuring improved minimal invasiveness in endoscopic surgery, and contributing to reduce uneven illumination distribution. The present technology provides an endoscopic image with reduced variation of uneven illumination distribution over time accompanied by pulsation of a living body or change in surgical field.

Also, the image under low illumination becomes dark as a whole. Therefore, the present technology corrects the image in such a manner as to increase brightness thereof to a level comparable to that of normal processing through synchronous signal processing. At this time, correction of the image brightness leads to increased noise. Therefore, synchronous signal processing is performed, and only the image under low illumination is subjected to a noise reduction (removal) process at a higher intensity, thus keeping the amount of noise at approximately the same level as a normal image.

Figure 1:
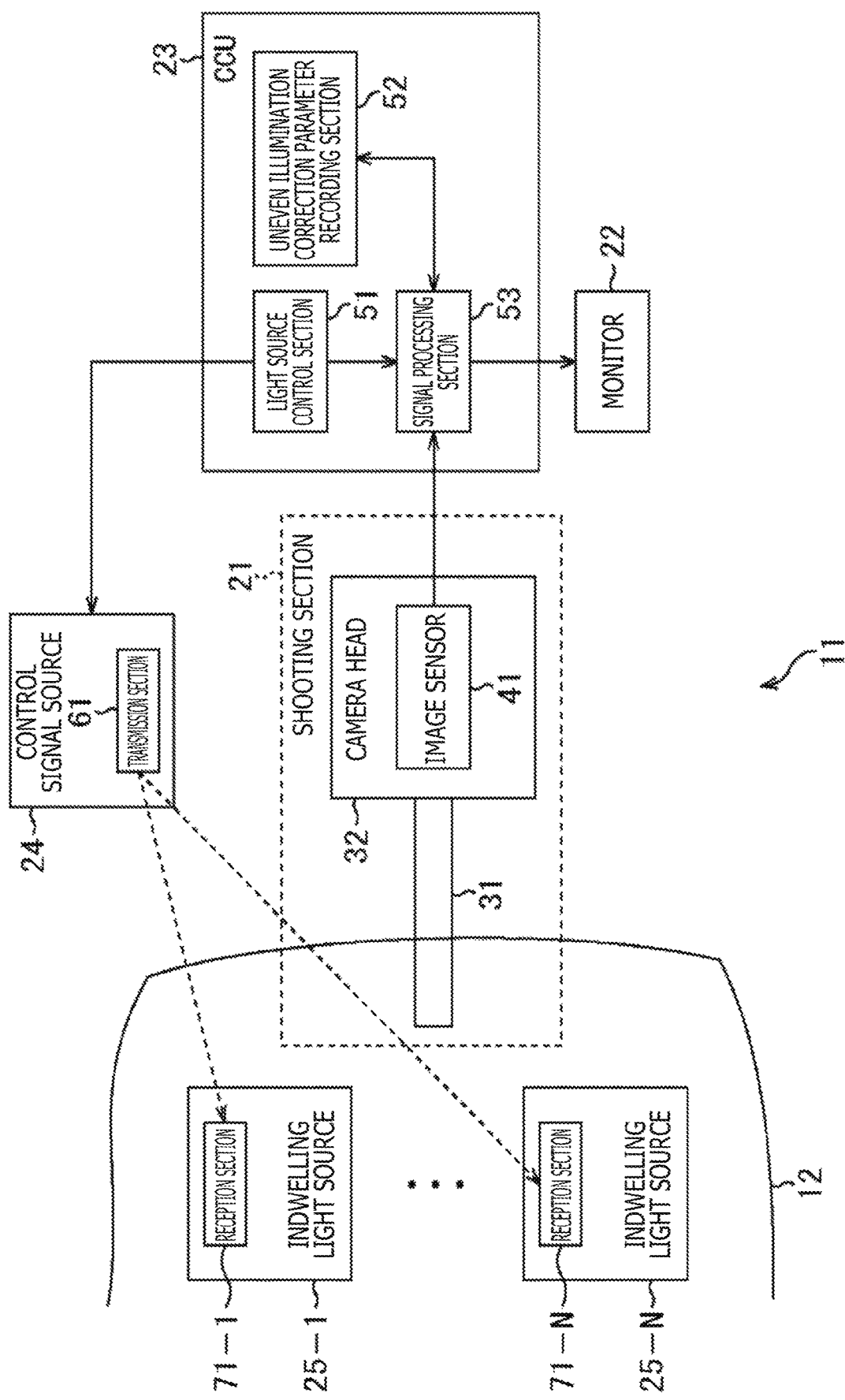
FIG. 1 is a diagram illustrating a configuration example of an endoscopic system.

FIG. 1 is a diagram illustrating a configuration example of an endoscopic system to which the present technology is applied.

An endoscopic system 11 is a system for operating on a surgical site such as affected site in a body cavity of a patient 12. The endoscopic system 11 includes a shooting section 21, a monitor 22, a CCU (Camera Control Unit) 23, a control signal source 24, and indwelling light sources 25-1 to 25-N. It should be noted that in a case where there is no particular need to distinguish between the indwelling light sources 25-1 to 25-N, the indwelling light sources 25-1 to 25-N will be simply referred to as the indwelling light sources 25.

The shooting section 21 includes a rigid endoscopic scope 31 and a camera head 32, shoots an image of a surgical site in a body cavity of the patient 12 (hereinafter also referred to as an endoscopic image), and supplies image data of the acquired endoscopic image to the CCU 23. That is, the shooting section 21 acquires image data of an endoscopic image by shooting a surgical site of the patient 12 to be operated on. It should be noted that although a case will be described here in which the endoscopic image is a video, the endoscopic image may be a still image.

In this example, the rigid endoscopic scope 31 is connected to the camera head 32, and the camera head 32 includes an image sensor 41.

Part of the rigid endoscopic scope 31 including a tip portion thereof is inserted into the patient 12 such that the tip portion is located near the surgical site. Also, the rigid endoscopic scope 31 includes an observation optics that includes lenses, focuses light from the surgical site, and guides the light to the camera head 32.

The image sensor 41 of the camera head 32 shoots the surgical site by receiving incident light from the surgical site via the rigid endoscopic scope 31 and converting the light into an electric current, outputting image data, acquired as a result thereof, to the CCU 23. That is, the image sensor 41 shoots an endoscopic image.

The monitor 22 includes a display apparatus such as LCD panel and displays an output image on the basis of the image data supplied from the CCU 23. For example, the output image is a video for observation acquired from the endoscopic image and used to observe the surgical site.

The CCU 23 controls all actions of the endoscopic system 11. The CCU 23 includes a light source control section 51, an uneven illumination correction parameter recording section 52, and a signal processing section 53.

The light source control section 51 supplies light source control information not only to the control signal source 24 but also to the signal processing section 53. The light source control information is used to control switching-on and switching-off of illumination by the indwelling light sources 25, and control illumination intensity (amount of light) of illuminating light, and so on. That is, the light source control section 51 controls, by means of light source control information, illumination of the surgical site of the patient 12 by the indwelling light sources 25.

The uneven illumination correction parameter recording section 52 records an uneven illumination correction parameter for correcting uneven illumination of the endoscopic image, a video. The uneven illumination correction parameter is calculated by the signal processing section 53. The uneven illumination correction parameter recording section 52 supplies, as necessary, the recorded uneven illumination correction parameter to the signal processing section 53.

The signal processing section 53 performs various signal processing tasks on the image data supplied from the image sensor 41 on the basis of the light source control information supplied from the light source control section 51.

For example, the signal processing section 53 calculates an uneven illumination correction parameter on the basis of the light source control information and the image data supplied from the image sensor 41, supplying the uneven illumination correction parameter to the uneven illumination correction parameter recording section 52 for recording.

Also, the signal processing section 53 performs, on the image data supplied from the image sensor 41, an uneven illumination correction process using the uneven illumination correction parameter, gain adjustment, a noise reduction process, and so on, thus generating image data of an output image depicting the surgical site, and the image data is provided to the monitor 22. Although a description has been given here by taking, as an example, a case in which the output image is a video acquired from an endoscopic image, the output image may be a still image.

The control signal source 24 includes a transmission section 61 and controls illumination by the indwelling light sources 25 in accordance with light source control information supplied from the light source control section 51.

That is, the control signal source 24 generates a light source control signal for instructing that illuminating light be shined (light be emitted) with a specified amount of light (at a specified illumination intensity) or that the shining of illuminating light be halted (light be extinguished). Also, the transmission section 61 of the control signal source 24 controls illumination actions of the indwelling light sources 25 by sending the generated light source control signal to the indwelling light sources 25 wirelessly (by electromagnetic wave).

The N indwelling light sources 25-1 to 25-N are light sources arranged (kept) near a surgical site in a body cavity of the patient 12 to shine illuminating light onto the surgical site of the patient 12.

The indwelling light sources 25-1 to 25-N include reception sections 71-1 to 71-N, respectively. These reception sections 71-1 to 71-N receive light source control signals sent from the control signal source 24 through wireless communication.

It should be noted that in a case where there is no particular need to distinguish between the reception sections 71-1 to 71-N, the reception sections 71-1 to 71-N will be simply referred to as the reception sections 71.

The indwelling light sources 25 shine illuminating light onto the affected site at the specified illumination intensity or halt the shining of illuminating light in accordance with the light source control signals received by the reception sections 71. That is, the indwelling light sources 25 perform actions such as switching-on and switching-off of illuminating light and so on under control of the control signal source 24 provided outside the body of the patient 12.

It should be noted that control over the indwelling light sources 25 is not limited to wireless control and may be performed through wired communication. Also, although a description has been given here of an example in which the plurality of indwelling light sources 25 are used, of course, the number of indwelling light sources 25 may be one.

As described above, the endoscopic system 11 illuminates the affected site by using the indwelling light sources 25 provided separately from the shooting section 21. In other words, illuminating light output from the indwelling light sources 25 is shined onto the affected site without going via the shooting section 21. This eliminates the need, in a portion of the rigid endoscopic scope 31, for illumination optics for irradiating illuminating light onto the affected site, i.e., a light guide for illuminating light, thus ensuring a reduced diameter of the rigid endoscopic scope 31 by as much as the size of the optics. As a result, minimal invasiveness in endoscopic surgery can be improved.

<Usage Example of Endoscopic System>

A description will be given here of a usage example of the endoscopic system 11 illustrated in FIG. 1 with reference to FIG. 2. It should be noted that components and portions in FIG. 2 corresponding to those in the case illustrated in FIG.

1 are denoted by the same reference signs, and description thereof will be omitted as appropriate.

Figure 2:
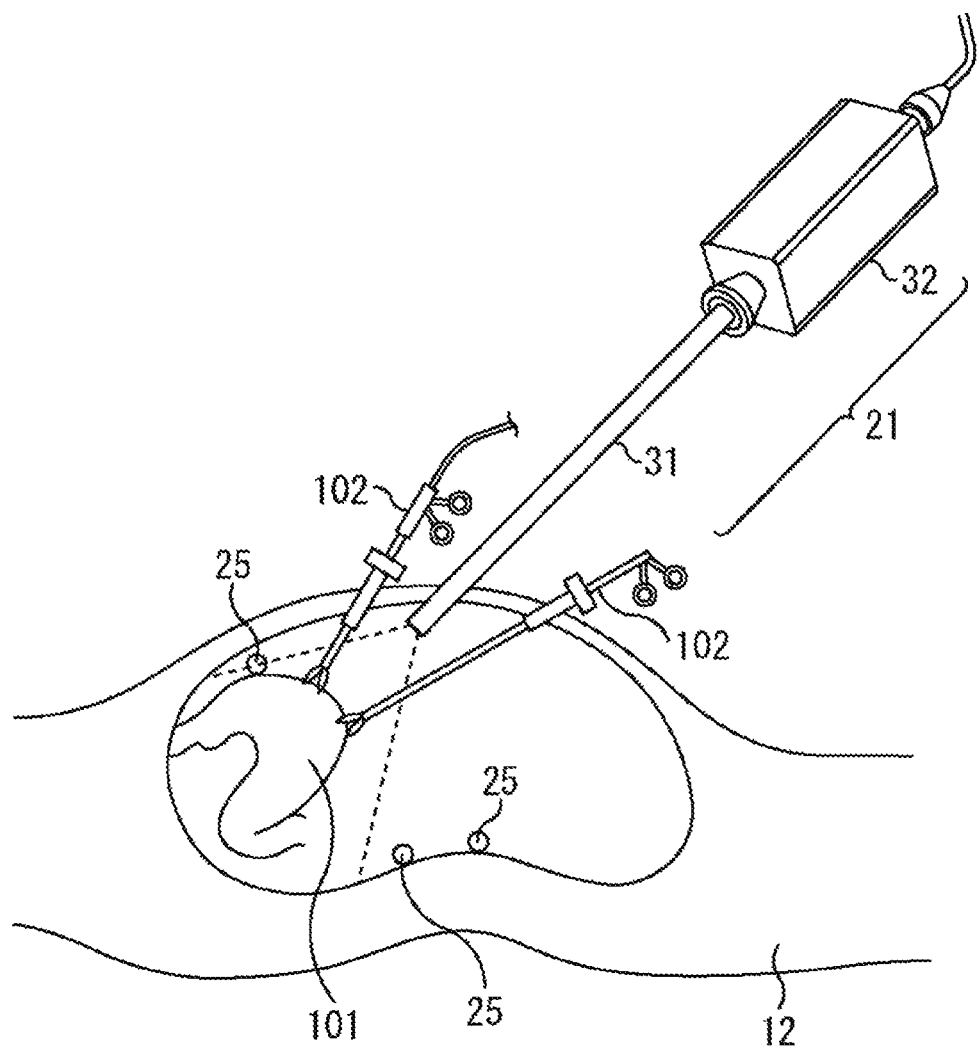
FIG. 2 is a diagram describing a usage example of the endoscopic system.

In the usage example illustrated in FIG. 2, the endoscopic system 11 shoots, for example, a surgical site 101, an area within the body to be operated on, as a subject and generates an output image on the basis of an endoscopic image depicting the subject. Then, the output image is supplied and displayed on the monitor 22, and a surgeon or the like conduct an endoscopic surgery to treat the surgical site 101 while watching the output image displayed on the monitor 22.

The rigid endoscopic scope 31 is inserted, for example, into a body cavity of the patient 12 (human body), and the camera head 32 shoots an endoscopic image of a tissue in the body cavity as a subject.

That is, the shooting section 21 includes, for example in appearance, the camera head 32 that is held in hand and manipulated by the practitioner (surgeon) engaging in the operation and the rigid endoscopic scope 31 in the form of a thin and long tube to be inserted into the body of the patient 12.

In an endoscopic surgery, for example, the rigid endoscopic scope 31, and forceps 102 as a treatment instrument, are inserted into the body of the patient 12.

Also, during operation, the surgical site 101 is illuminated by the indwelling light sources 25 kept in the body cavity of the patient 12. In the shooting section 21, illuminating light reflected by the surgical site 101, i.e., reflected light of the illuminating light, enters the rigid endoscopic scope 31 from the tip thereof and is received by the image sensor 41, thus allowing the surgical site 101 to be shot as a subject.

In this example, the plurality of indwelling light sources 25 are inserted into the body cavity of the patient 12 in advance from a wound or other part for inserting the rigid endoscopic scope 31 and kept at positions near the surgical site 101 in the body cavity. For example, the indwelling light sources 25 may be fastened with clips or the like.

It should be noted that although an example has been described in FIG. 2 in which each of the indwelling light sources 25 is kept at a position near the surgical site 101 in the body cavity of the patient 12, the indwelling light sources 25 may be arranged in any manner as long as the indwelling light sources 25 are arranged in such a manner as to illuminate the surgical site 101, a subject, properly.

Figure 3:
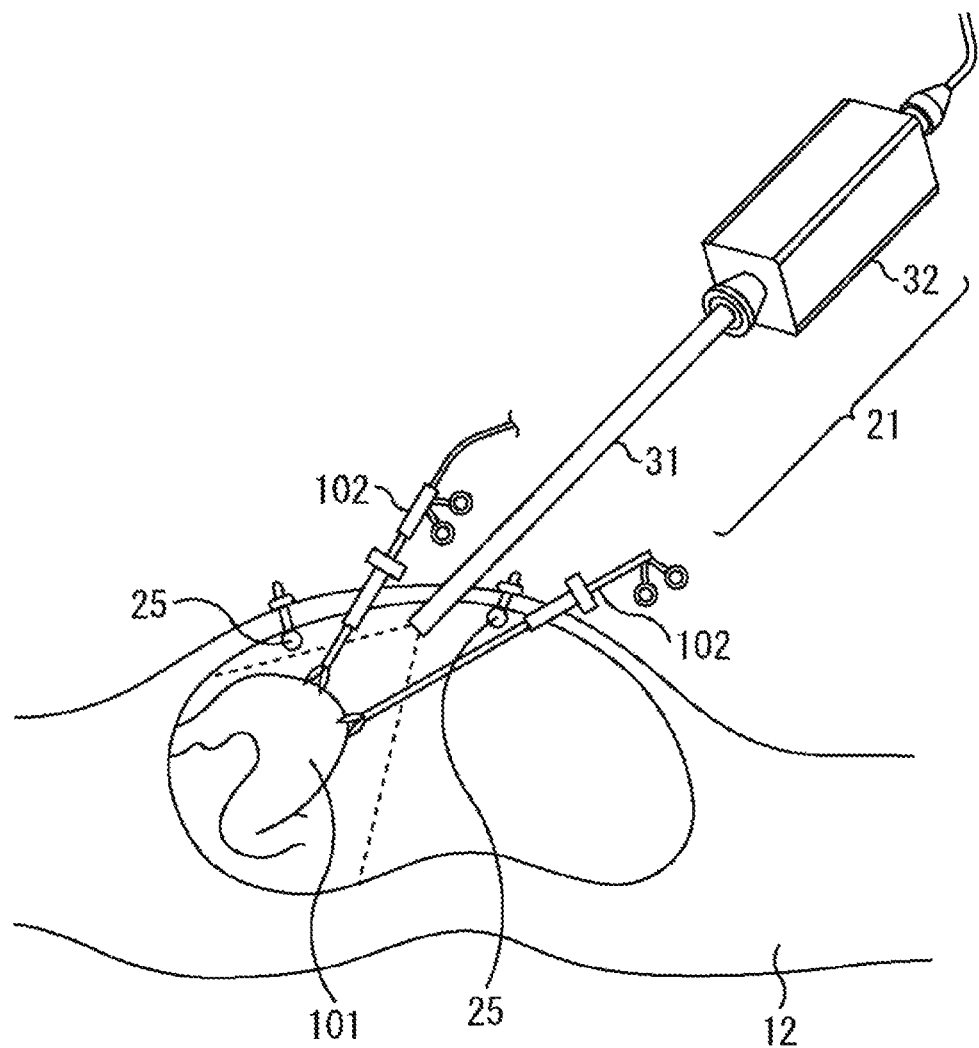
FIG. 3 is a diagram describing a usage example of the endoscopic system.

For example, each of the indwelling light sources 25 may be fastened to a fastener inserted in the patient 12 as illustrated in FIG. 3. It should be noted that components and portions in FIG. 3 corresponding to those in the case illustrated in FIG. 2 are denoted by the same reference signs, and description thereof will be omitted as appropriate.

In the example illustrated in FIG. 3, the fasteners are inserted and fastened in the patient 12, and the indwelling light sources 25 are fastened to the fasteners, thus allowing each of the plurality of indwelling light sources 25 to be arranged near the surgical site 101 in the body cavity.

In addition to the above, for example, a unidirectionally long illuminating light source may be used as the indwelling light source 25 and inserted into the body cavity of the patient 12 and fastened therein. Alternatively, the indwelling light sources 25 may be fastened to the two pairs of forceps 102 by using some kind of strings.

<Uneven Illumination Correction>

A description will be given next of occurrence of uneven illumination and correction of such uneven illumination during shooting of an endoscopic image.

Figure 4:
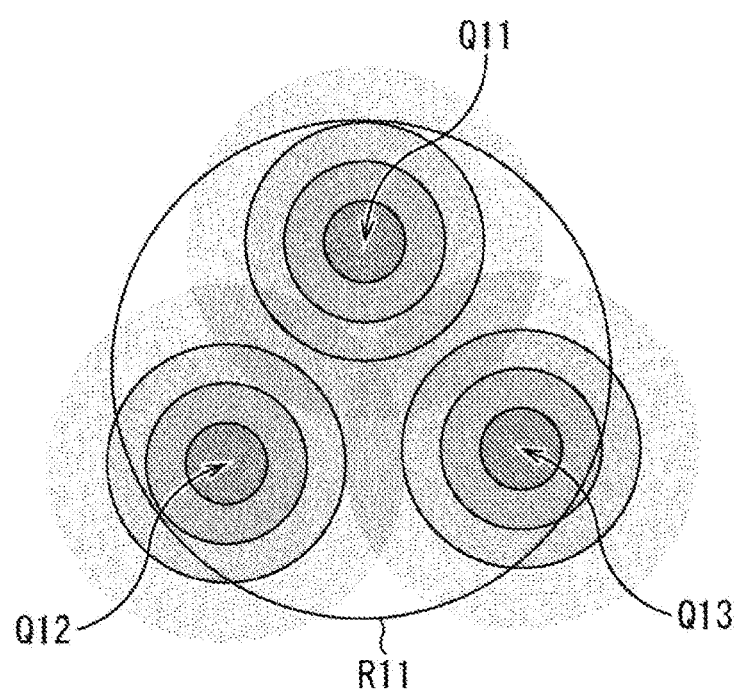
FIG. 4 is a diagram describing uneven illumination.

In a case where a surgical site is illuminated by the plurality of indwelling light sources 25, uneven illumination, i.e., uneven illumination distribution, occurs near the surgical site as illustrated, for example, in FIG. 4.

In the example illustrated in FIG. 4, a circular region R11 represents a region of an observation field of view for the rigid endoscopic scope 31 in the surgical site.

Also, concentric circles having a center at a position indicated by an arrow Q11 depict the manner in which the surgical site is illuminated by one of the indwelling light sources 25. Similarly, concentric circles having centers at positions indicated respectively by arrows Q12 and Q13 depict the manner in which the surgical site is illuminated by the other indwelling light sources 25 different from each other. Here, shading of each region represents illumination intensity, i.e., illumination intensity distribution, produced by illuminating light.

As described above, when the surgical site is illuminated by the plurality of indwelling light sources 25, the illumination intensity varies between different positions of the region R11 of the observation field of view of the surgical site, thus resulting in uneven illumination. In particular, the illumination intensity in each region of the surgical site shined with illuminating light varies depending on the illumination intensity of the indwelling light sources 25 themselves, i.e., the amount of illuminating light, distances from the indwelling light sources 25 to the surgical site, and other factors.

Also, during shooting of an endoscopic image, a shape of the surgical site changes as a result of pulsation of the patient 12 to be operated on (living body), surgery, or other cause.

Figure 5:
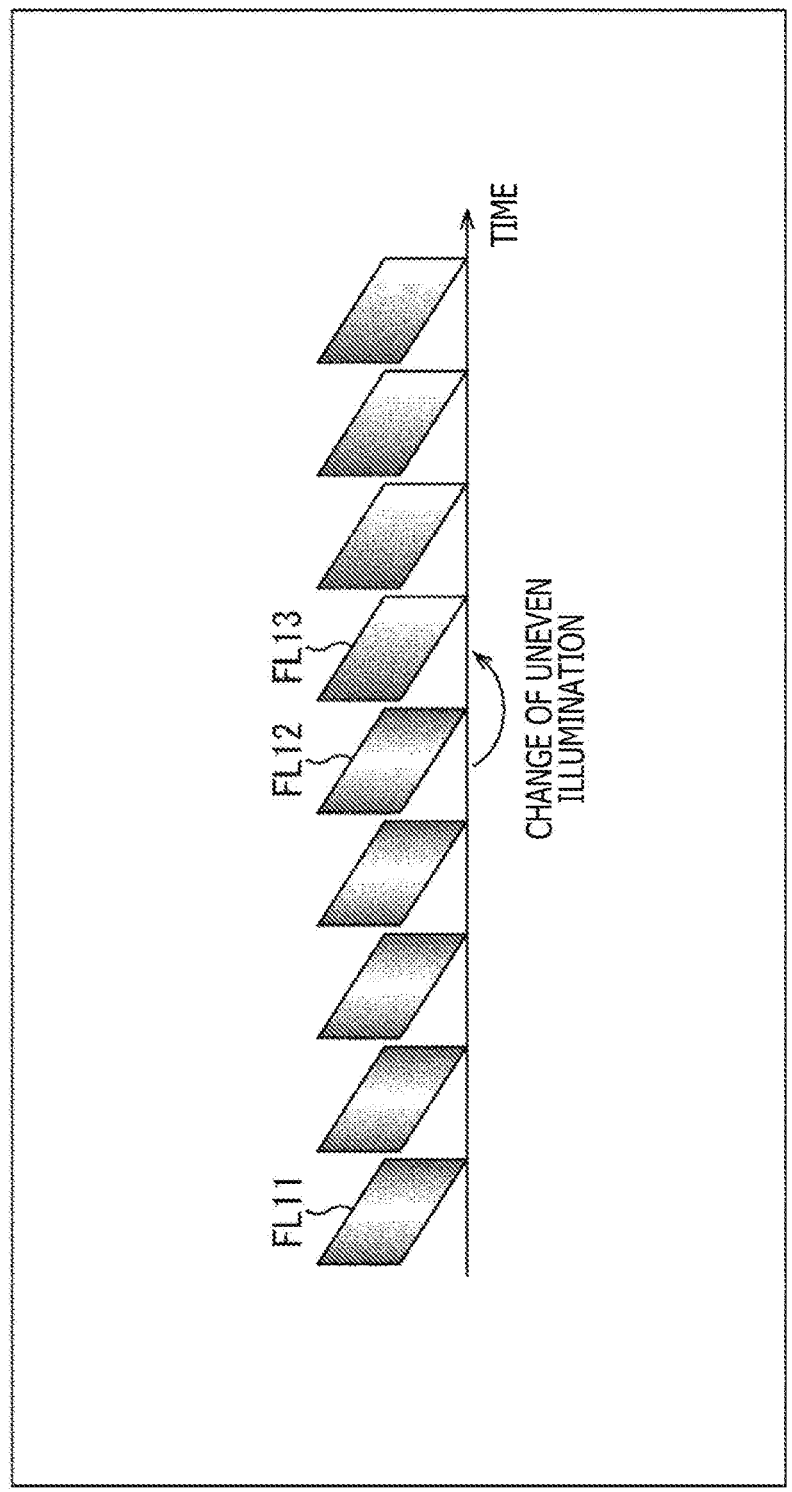
FIG. 5 is a diagram describing a change of uneven illumination over time.

Therefore, as the distances from the indwelling light sources 25 to the surgical site, the positional relationship between the surgical site and each of the indwelling light sources 25, and other factors change over time due to the change in shape of the surgical site, for example, uneven illumination also varies in the time direction as illustrated in FIG. 5.

It should be noted that a horizontal direction in FIG. 5 represents time and that each rectangle represents a frame of an endoscopic image as a video. Also, the shading at each position of the frame represents illumination intensity, i.e., pixel luminance value at each position.

In this example, the respective consecutive frames from a first frame FL11 to a frame FL12 have approximately the same uneven illumination distribution, in other words, illumination intensity distribution. However, the frame FL12 and a next frame FL13 have significantly different uneven illumination distributions. As described above, in an endoscopic image, not only its illumination intensity (luminance) but also its illumination intensity distribution vary over time between different regions of the frame.

Figure 6:
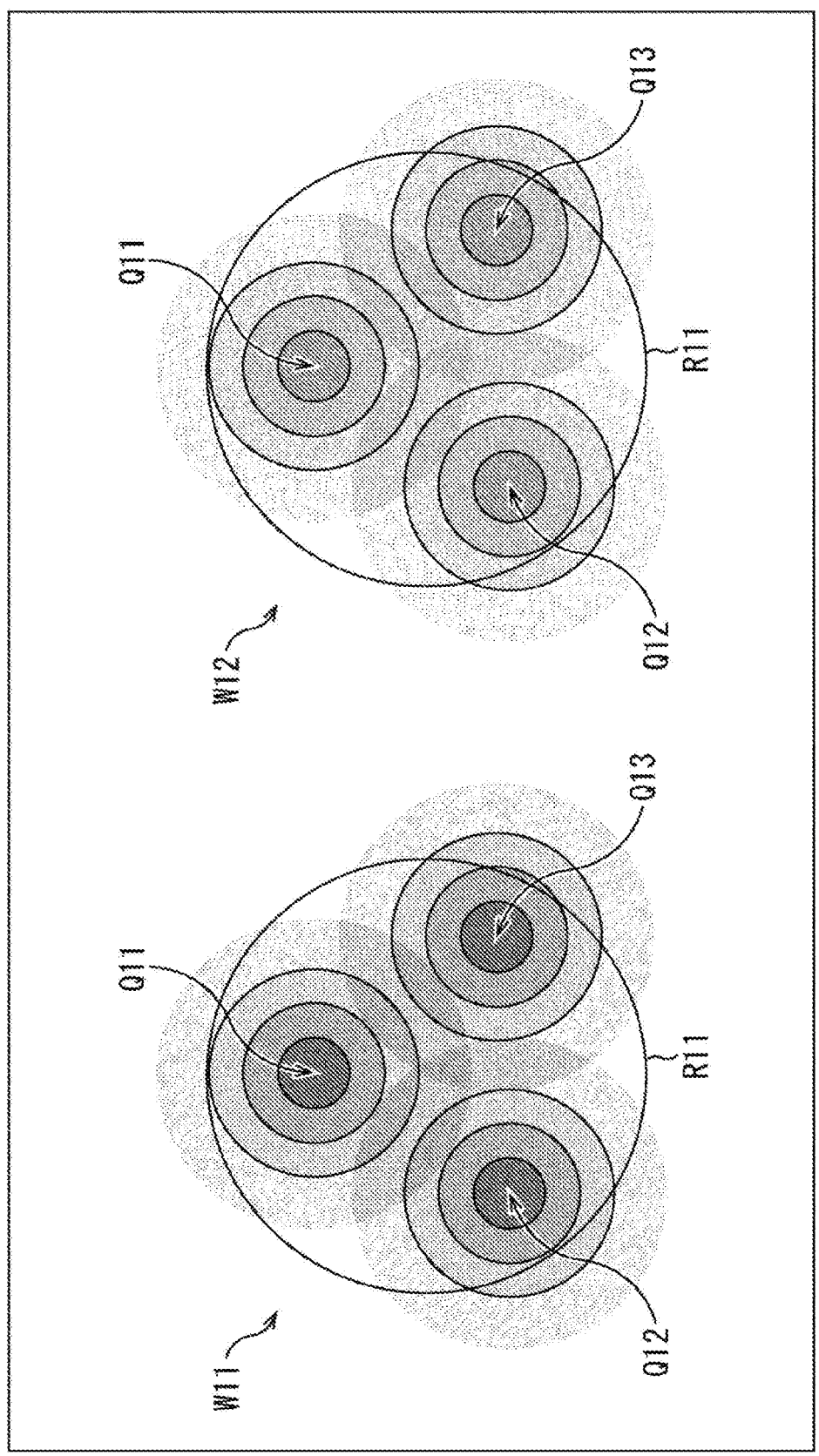
FIG. 6 is a diagram describing illumination control.

For this reason, the endoscopic system 11 performs control, for example, as illustrated in FIG. 6 such that the illumination intensity (amount of illuminating light) of each of the indwelling light sources 25 is reduced lower than the normal illumination intensity only for a one-frame-long shooting time period of the endoscopic image at a constant time interval, thus calculating an uneven illumination correction parameter by using frames (images) having different illumination intensities. It should be noted that components and portions in FIG. 6 corresponding to those in the case illustrated in FIG. 4 are denoted by the same reference signs, and description thereof will be omitted as appropriate.

In the portion indicated by an arrow W11 in FIG. 6, an illumination intensity distribution at the surgical site is depicted when the surgical site is illuminated by each of the indwelling light sources 25 at a predetermined illumination intensity (hereinafter also referred to as a normal illumination intensity). In this example, although having uneven illumination, the respective regions are brightly illuminated.

In contrast, the portion indicated by an arrow W12 in FIG. 6 depicts an illumination intensity distribution at the surgical site when the surgical site is illuminated by each of the indwelling light sources 25 at an illumination intensity lower than the normal illumination intensity (hereinafter also referred to as a low illumination intensity). In this example, the surgical site is darker because of an illumination intensity lower than during illumination at the normal illumination intensity. However, the surgical site has less uneven illumination compared to during illumination at the normal illumination intensity. That is, the respective regions of the surgical site are approximately uniformly illuminated.

It should be noted that the illumination intensity may be zero during illumination at the low illumination intensity, that is, each of the indwelling light sources 25 may be switched off so that shining with illuminating light (illumination) is halted. Also, during illumination at the low illumination intensity, each of the indwelling light sources 25 may be set to any illumination intensity as long as the overall intensity of illumination produced by the plurality of indwelling light sources 25 is lower than during illumination at the normal illumination intensity. The description will be continued below by assuming that illumination is conducted at a given illumination intensity lower than the normal illumination intensity but higher than zero.

The endoscopic system 11 performs control such that an endoscopic image is basically shot under illumination at the normal illumination intensity and shot under illumination at the lower illumination intensity only for one-frame-long shooting time at a constant time interval.

When controlling the illumination intensity, the light source control section 51 generates light source control information for instructing that illuminating light be shined at the normal or low illumination intensity and supplies the light source control information to the control signal source 24 and the signal processing section 53. Also, the control signal source 24 generates a light source control signal proportional to the light source control information and controls the illumination produced by the indwelling light sources 25 by wirelessly sending the light source control signal.

Figure 7:
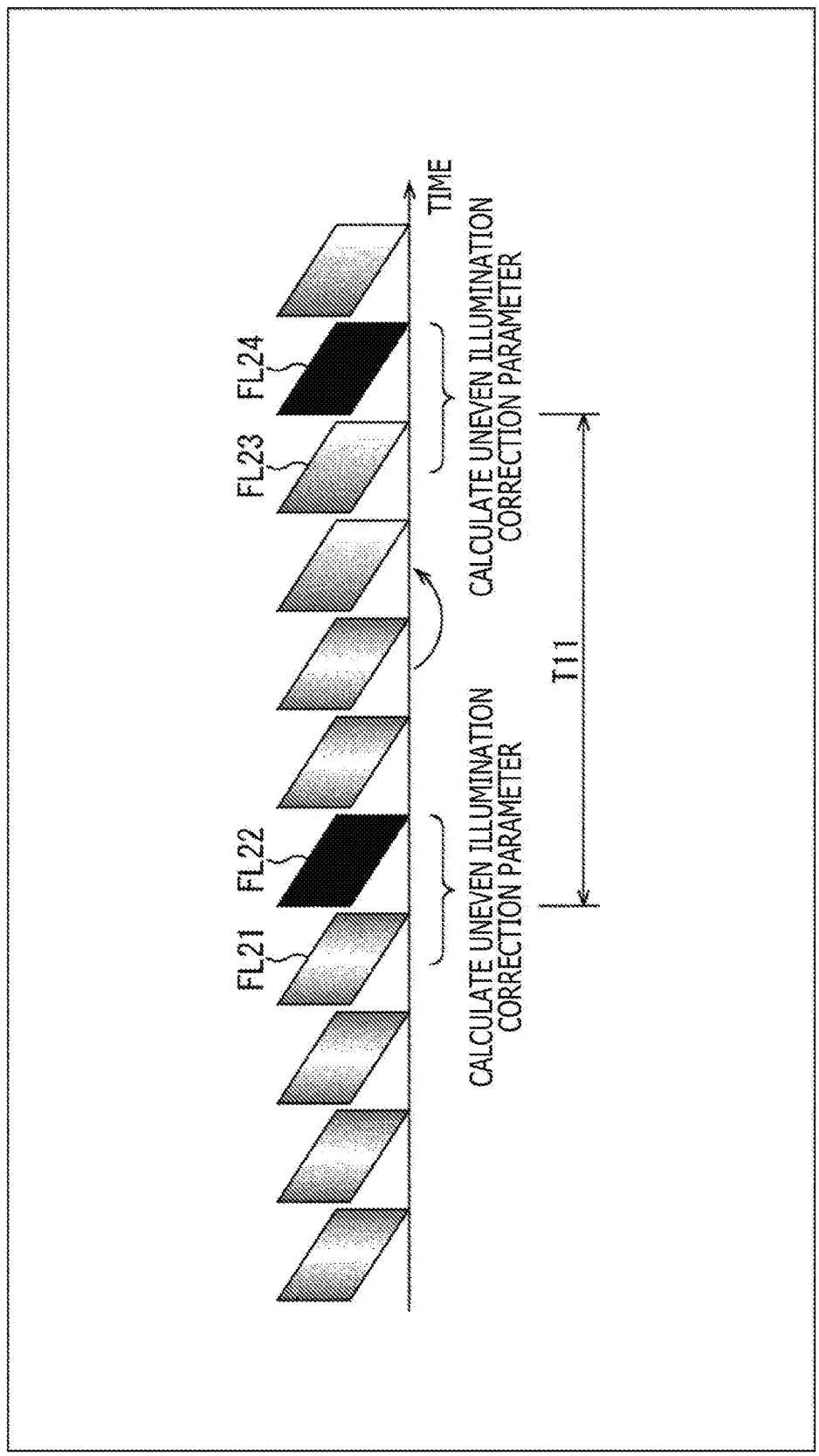
FIG. 7 is a diagram describing calculation of an uneven illumination correction parameter.

As a result, an endoscopic image illustrated, for example, in FIG. 7 is acquired. It should be noted that the horizontal direction in FIG. 7 represents time and that each rectangle represents a frame of an endoscopic image as a video. Also, the shading at each position of the frame represents illumination intensity, i.e., pixel luminance value at each position.

In the example illustrated in FIG. 7, illumination is conducted at the low illumination intensity during shooting periods of frames FL22 and FL24 whereas illumination is conducted at the normal illumination intensity during shooting periods of frames other than the frames FL22 and FL24, thus allowing each frame to be shot.

It should be noted that although an example has been described here in which illumination is conducted at the low illumination intensity at a given interval, i.e., regularly, illumination at the low illumination intensity may be conducted irregularly.

If an endoscopic image is shot with the illumination intensity switched in such a manner that illumination is conducted at the low illumination intensity at a constant interval as described above, the endoscopic system 11 calculates an uneven illumination correction parameter on the basis of a frame illuminated at the low illumination intensity and a frame illuminated at the normal illumination intensity near the frame illuminated at the low illumination intensity.

In other words, uneven illumination of an endoscopic image is corrected on the basis of an image (frame) of a surgical site shot by the shooting section 21 with the surgical site illuminated at the normal illumination intensity by the indwelling light sources 25 and an image (frame) of the surgical site shot by the shooting section 21 with the surgical site illuminated at an illumination intensity lower than the normal illumination intensity.

Specifically, for example, the endoscopic system 11 calculates an uneven illumination correction parameter to be used during a period T11 on the basis of frames FL21 and FL22 adjacent to each other. The frame FL21 is illuminated at the normal illumination intensity, and the frame FL22 is illuminated at the low illumination intensity. It should be noted that, in addition to the above, an uneven illumination correction parameter may be calculated by using, for example, the frame FL22 and its succeeding frame.

Here, a frame shot under illumination at the normal illumination intensity in particular will be also referred to as a normally illuminated frame, and a frame shot under illumination at the low illumination intensity in particular will be also referred to as a low illuminated frame.

By using two frames with different illumination intensities (luminances), namely, a bright normally illuminated frame that was illuminated at the normal illumination intensity and a low illuminated frame with minimal uneven illumination, it is possible to acquire an appropriate uneven illumination correction parameter. It should be noted that although calculated for each pixel of an endoscopic image, an uneven illumination correction parameter may be calculated for each region that includes adjacent pixels of an endoscopic image.

The uneven illumination correction parameter acquired as described above is supplied from the signal processing section 53 to the uneven illumination correction parameter recording section 52 for recording. Then, the uneven illumination correction process is performed later by using the uneven illumination correction parameter recorded in the uneven illumination correction parameter recording section 52.

That is, in the example illustrated in FIG. 7, for example, the uneven illumination correction process is performed on each of the frames during the period T11 by using the uneven illumination correction parameter calculated from the frames FL21 and FL22 and recorded in the uneven illumination correction parameter recording section 52.

Here, the period T11 is a period lasting from the frame FL22, a low illuminated frame, to the frame FL23, a frame immediately previous to the next low illuminated frame FL24.

Similarly, the endoscopic system 11 calculates an uneven illumination correction parameter to be used for the frame FL24 onward on the basis of the frame FL23, a normally illuminated frame, and the frame FL24, a low illuminated frame. Then, the calculated uneven illumination correction parameter is supplied to the uneven illumination correction parameter recording section 52 for recording. That is, the uneven illumination correction parameter recorded in the uneven illumination correction parameter recording section 52 is updated.

As described above, the endoscopic system 11 calculates (updates) an uneven illumination correction parameter when a low illuminated frame is acquired. Then, the acquired uneven illumination correction parameter is applied to each frame while a next low illuminated frame is acquired, that is, while the uneven illumination correction parameter is updated.

Also, more particularly, when generating an output image, the endoscopic system 11 performs not only the uneven illumination correction process but also the gain adjustment process and the noise reduction process.

Figure 8:
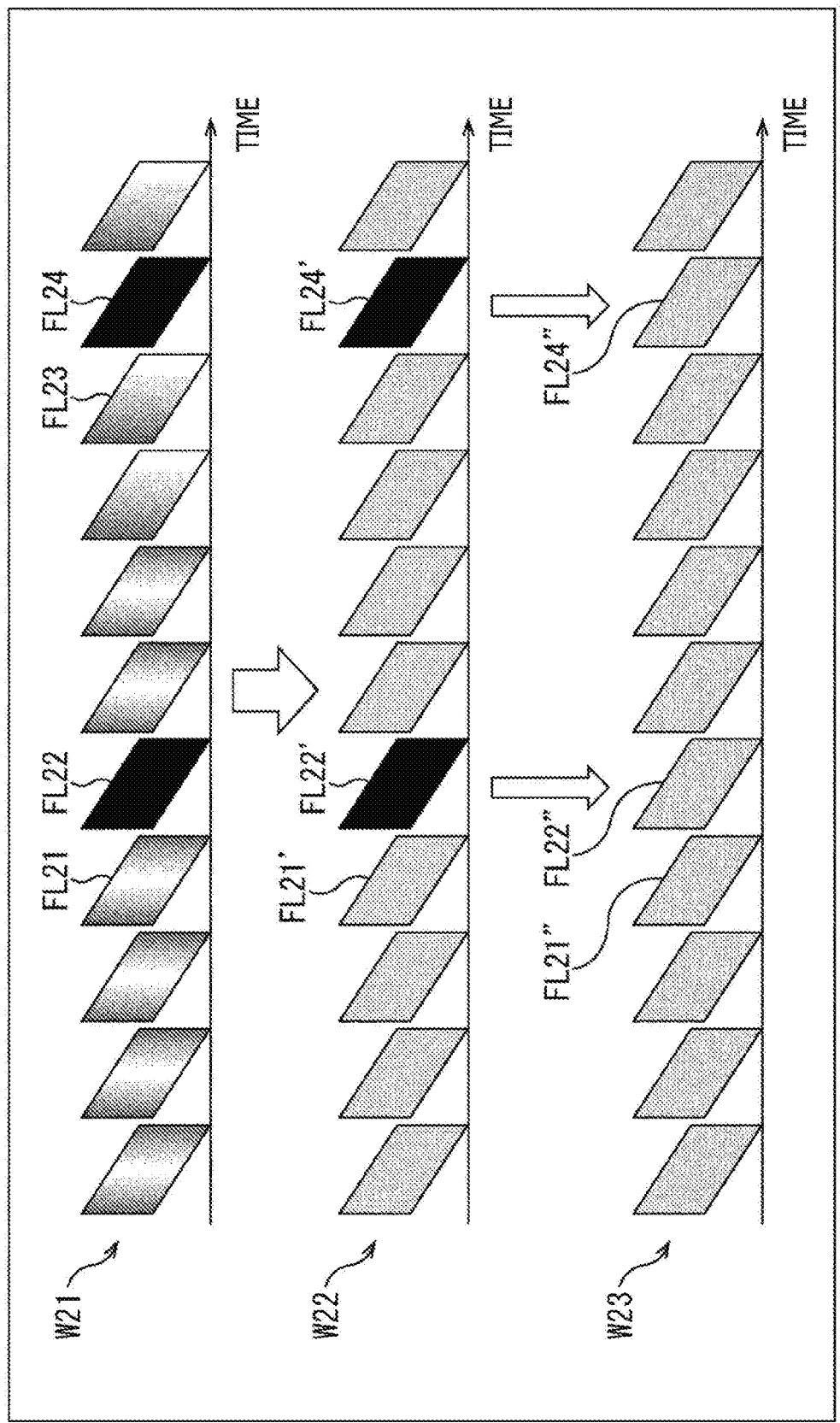
FIG. 8 is a diagram describing correction of the uneven illumination.

We assume, for example, that an endoscopic image is acquired that includes consecutive frames at different times of day as indicated by an arrow W21 in FIG. 8. It should be noted that components and portions in FIG. 8 corresponding to those in the case illustrated in FIG. 7 are denoted by the same reference signs, and description thereof will be omitted as appropriate. Also, the horizontal direction in FIG. 8 represents time, and each rectangle represents a frame of an endoscopic image as a video. Further, the shading at each position of the frame represents illumination intensity, i.e., pixel luminance value at each position.

For example, if the endoscopic image indicated by the arrow W21 is acquired, an uneven illumination correction parameter is calculated when a low illuminated frame is acquired.

As a result, the uneven illumination correction process is performed on each of the frames by using the calculated uneven illumination correction parameter. In the uneven illumination correction process, for example, the pixel value of each of the pixels of a target frame is multiplied by the uneven illumination correction parameter corresponding to the pixel, thus correcting the uneven illumination in the frame.

The endoscopic image indicated by an arrow W22 represents an endoscopic image all of whose frames have undergone the uneven illumination correction process. In this example, uneven illumination has been corrected in each frame, thus providing frames free from uneven illumination and having an appropriate illumination distribution.

Specifically, in the endoscopic image indicated by the arrow W22, for example, a frame FL21' represents a frame acquired as a result of the uneven illumination correction process performed on the frame FL21, and a frame FL22' represents a frame acquired as a result of the uneven illumination correction process performed on the frame FL22. Also, a frame FL24' represents a frame acquired as a result of the uneven illumination correction process performed on the frame FL24.

The uneven illumination correction process is followed, as appropriate, by the gain adjustment process, and further, by the noise reduction process on each frame, thus providing an output image indicated by an arrow W23. It should be noted that, in more detail, each frame is selected in sequence as a target and that the target frame is subjected to the uneven illumination correction process and the noise reduction process. That is, each frame is processed in sequence.

Here, for example, a frame FL21" acquired as a result of the noise reduction process performed on the frame FL21' is a frame of the output image corresponding to the frame FL21 of the endoscopic image. Also, a frame FL22" acquired as a result of the gain adjustment process and the noise reduction process performed on the frame FL22' is a frame of the output image corresponding to the frame FL22 of the endoscopic image. Similarly, a frame FL24" acquired as a result of the gain adjustment process and the noise reduction process performed on the frame FL24' is a frame of the output image corresponding to the frame FL24 of the endoscopic image.

In particular, the output image indicated by the arrow W23 is a bright video whose uneven illumination has been corrected in each frame and that has approximately the same luminance in each frame.

Specifically, the gain adjustment process is performed on the low illuminated frames whose overall luminance is lower, i.e., the frames that are darker than the normally illuminated frames such that low illuminated frames are equal in overall brightness (luminance) to the normally illuminated frames. In contrast, no gain adjustment process is performed on the normally illuminated frames.

It should be noted that a gain value used for the gain adjustment process need only be calculated in advance on the basis of a ratio between the normal illumination intensity and the low illumination intensity or other value. In addition to the above, a gain value may be calculated from the difference or ratio between a mean luminance value of all the normally illuminated frames and that of all the low illuminated frames, for example, during calculation of an uneven illumination correction parameter.

Here, the gain adjustment process is performed only on the low illuminated frames because the low illuminated frames are darker as a whole than the normally illuminated frames and, therefore, the uneven illumination correction process alone produces an output image that is dark at each time interval when the illumination intensity is switched. The endoscopic system 11 achieves approximately the same luminance for all frames of the image through gain adjustment of the low illuminated frames.

Also, the normally illuminated frames that have not been subjected to the gain adjustment process and the low illuminated frames that have been subjected to the gain adjustment process undergo, as noise reduction processes, filtering processes, each using a given NR filtering factor. These frames are used as frames of the output image.

It should be noted that the noise reduction processes on the normally illuminated frames and the low illuminated frames can be performed at different processing intensities.

For example, the luminance of the low illuminated frames reaches a level comparable to that of the normally illuminated frames as a result of the gain adjustment process described above. However, the low illuminated frames are frames originally shot under illumination at a lower-than-normal illumination intensity. Therefore, noise is emphasized by the gain adjustment process.

For this reason, the noise reduction process may be performed on the low illuminated frames at a higher processing intensity than on the normally illuminated frames so as to provide an image whose low illuminated frames have a luminance level (brightness) and sense of noise comparable to those of the normally illuminated frames.

Specifically, in order to adjust the processing intensity of the noise reduction process, for example, it is only required to use processing intensity adjustment factors for adjusting the processing intensity. We assume, for example, that a normal intensity adjustment factor, a processing intensity adjustment factor for adjusting the processing intensity of the noise reduction process to a normal processing intensity, and a high intensity adjustment factor, a processing intensity adjustment factor for adjusting the processing intensity of the noise reduction process to a higher-than-normal processing intensity, are made available in advance.

In this case, the signal processing section 53 performs the noise reduction process on the low illuminated frames by using a factor acquired by multiplying the NR filtering factor by the high intensity adjustment factor. Also, the signal processing section 53 performs the noise reduction process on the normally illuminated frames by using a factor acquired by multiplying the NR filtering factor by the normal intensity adjustment factor.

As a result, the noise reduction process is performed on the low illuminated frames at a higher processing intensity than on the normally illuminated frames, thus reducing noise to a greater extent.

It should be noted that the processing intensity of the noise reduction process may be adjusted in any manner such as by varying a tap range of the NR filtering factor used for the noise reduction process rather than by multiplying the NR filtering factor by the high intensity adjustment factor or the normal intensity adjustment factor.

As described above, in a case where a surgical area in a body cavity of the patient 12 is shot by using illuminating light produced by the indwelling light sources 25, the endoscopic system 11 provides an output image with reduced uneven illumination involving variation over time, i.e., reduced uneven illumination distribution.

<Uneven Illumination Correction Parameter>

A description will be given here of a specific calculation example of the uneven illumination correction parameter described above.

Figure 9:
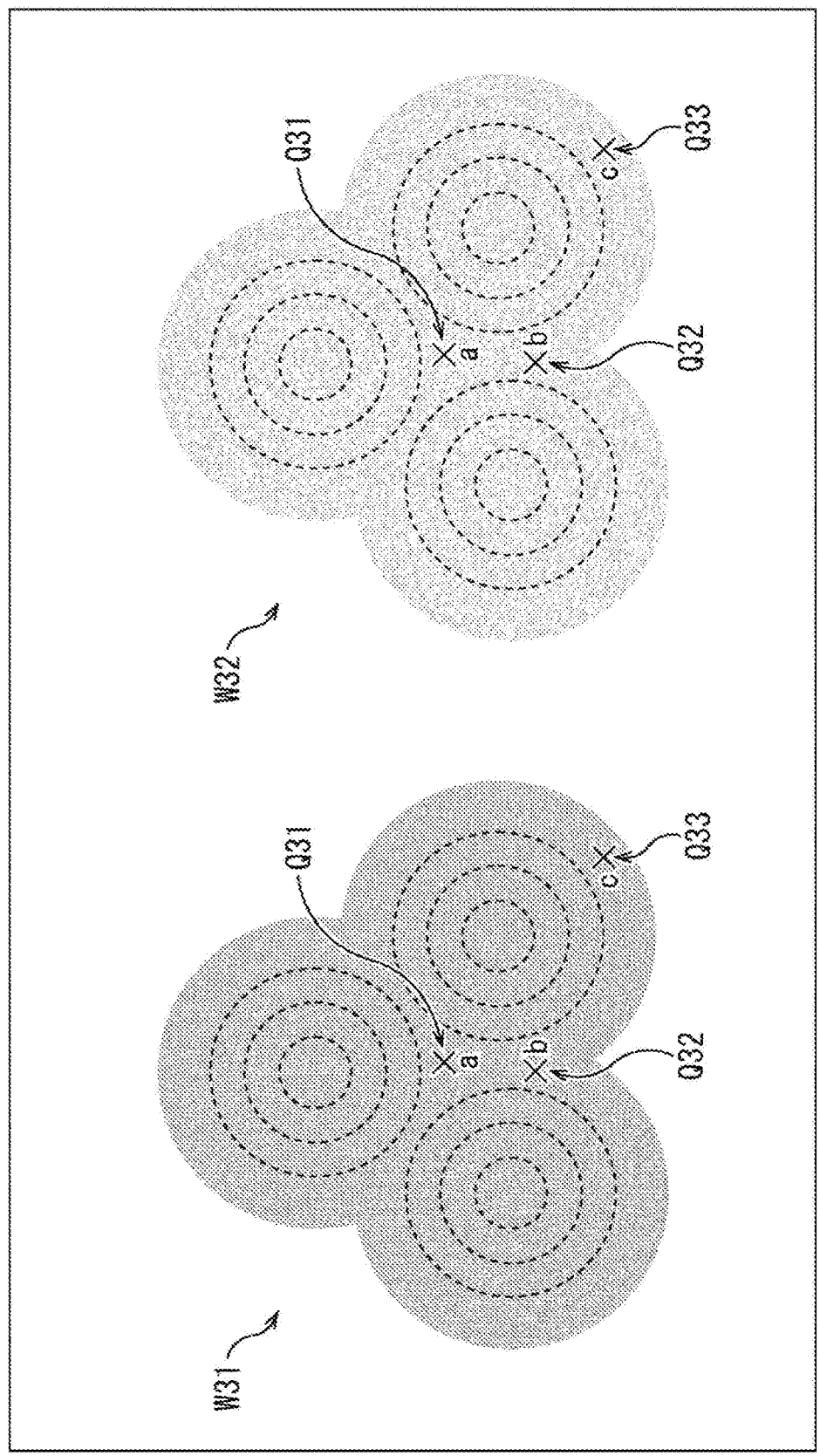
FIG. 9 is a diagram describing the calculation of the uneven illumination correction parameter.

We assume, for example, that no uneven illumination is present under illumination produced by the indwelling light sources 25 and that illumination distributions as illustrated in FIG. 9 are acquired by illumination produced at the normal illumination intensity and that at the low illumination intensity.

It should be noted that the portion indicated by an arrow W31 in FIG. 9 represents an illumination intensity distribution in a surgical site when the surgical site is illuminated by each of the indwelling light sources 25 at the normal illumination intensity. Also, the portion indicated by an arrow W32 represents an illumination intensity distribution in the surgical site when the surgical site is illuminated by each of the indwelling light sources 25 at the low illumination intensity.

Further, in the portions indicated by the arrows W31 and W32, each of the concentric circles depicts the manner in which the surgical site is illuminated by one of the indwelling light sources 25. The shading of each region represents illumination intensity produced by illuminating light.

In the example illustrated in FIG. 9, no uneven illumination is present. Therefore, the portion indicated by the arrow W31 has a uniform overall illumination intensity distribution, i.e., a uniform luminance distribution. As a result, a bright endoscopic image having uniform luminance is acquired if an endoscopic image of this surgical site is shot as a subject. Similarly, the portion indicated by the arrow W32 has a uniform overall illumination intensity distribution, i.e., a uniform luminance distribution although dark as a whole due to illumination at the low illumination intensity.

Here, respective positions of the surgical site indicated by arrows Q31 to Q33 will be also referred to as observation points "a" to "c."

For example, the observation point "a" indicated by the arrow Q31 is located at the approximate center of the observation field of the rigid endoscopic scope 31, and the observation point "b" indicated by the arrow Q32 is located below the observation point "a" in the figure. Also, the observation point "c" indicated by the arrow Q33 is located below and to the right of the observation point "a" in the figure.

Further, in the frame of the endoscopic image shot in an illumination condition indicated by the arrow W31, i.e., the endoscopic image shot under illumination at the normal illumination intensity, the luminance values of the pixels at the observation points "a" to "c" will be denoted as luminance values $I_a'$, $I_b'$, and $I_c'$, respectively.

Also, in the frame of the endoscopic image shot in an illumination condition indicated by the arrow W32, i.e., the endoscopic image shot under illumination at the low illumination intensity, the luminance values of the pixels at the observation points "a" to "c" will be denoted as luminance values $I_a$, $I_b$, and $I_c$, respectively. It should be noted that the same observation point in a normally illuminated frame and a low illuminated frame adjacent to each other in time is located at the pixel position having the same positional relationship. That is, assuming, for example, that the observation point "a" is located at the center position of the frame in the normally illuminated frame, the observation point "a" is located at the center position of the frame in the low illuminated frame.

In this example, no uneven illumination is present. Therefore, the rate of increase in luminance value (pixel value) at the same position of a frame of the endoscopic image under illumination at the normal illumination intensity relative to the frame of the endoscopic image under illumination at the low illumination intensity is constant irrespective of the position of the frame of the endoscopic image, i.e., the position of the observation point.

Therefore, $(I_a'-I_a)/I_a=(I_b'-I_b)/I_b=(I_c'-I_c)/I_c$ holds for the observation points "a" to "c," and if, for example, the luminance values $I_a$ and $I_b$ are equal ($I_a=I_b$), the luminance values $I_a'$ and $I_b'$ are equal ($I_a'=I_b'$).

Here, for example, $(I_a'-I_a)/I_a$ represents the rate of increase in the luminance value $I_a'$ of the normally illuminated frame relative to the luminance value $I_a$ of the low illuminated frame at the observation point "a," i.e., the rate of change in luminance between the low illuminated frame and the normally illuminated frame.

Figure 10:
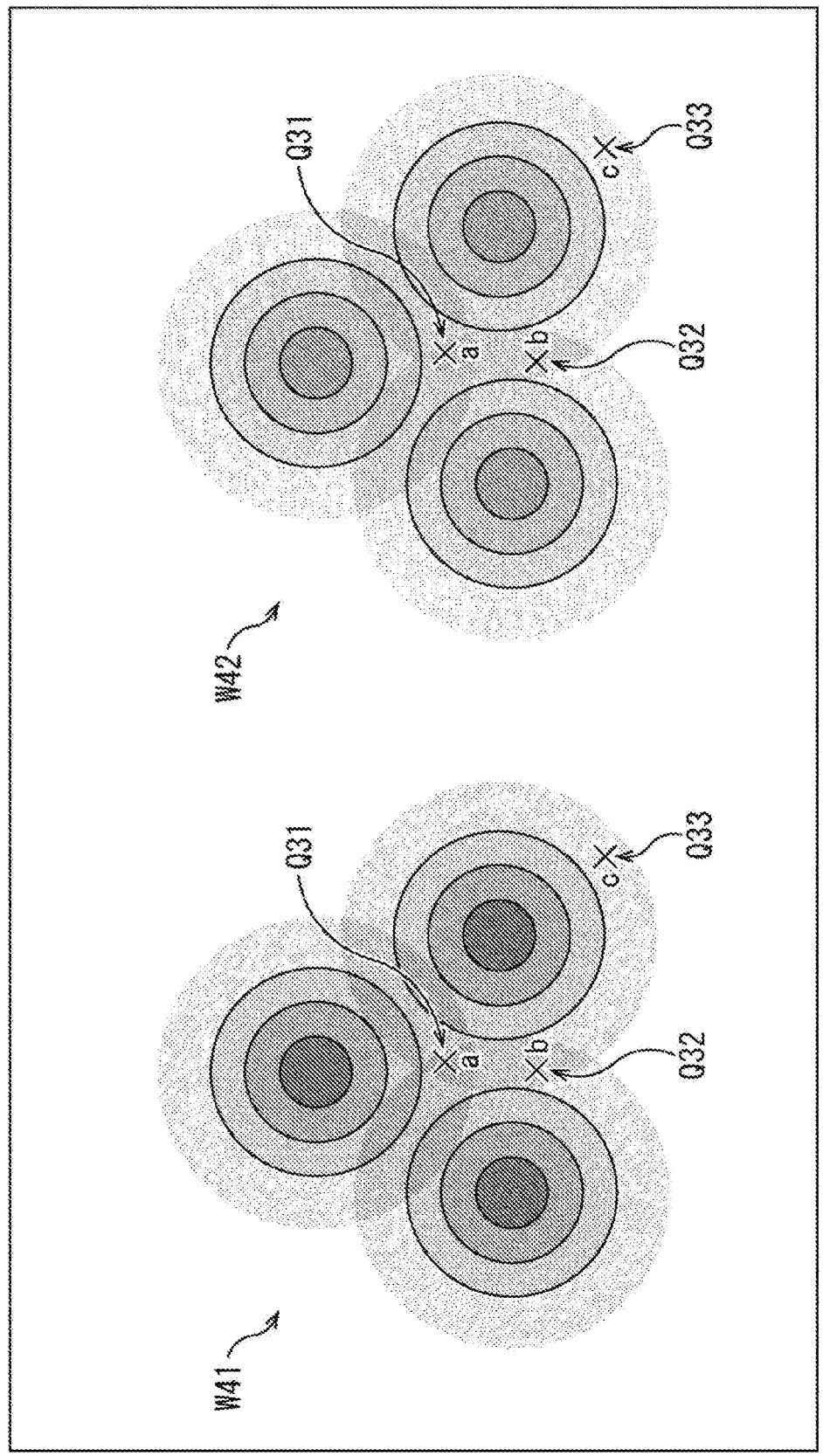
FIG. 10 is a diagram describing the calculation of the uneven illumination correction parameter.

On the other hand, assuming that uneven illumination is present due to illumination produced by the indwelling light sources 25, illumination distributions as illustrated, for example, in FIG. 10 are acquired by illumination produced at the normal illumination intensity and that at the low illumination intensity. It should be noted that components and portions in FIG. 10 corresponding to those in the case illustrated in FIG. 9 are denoted by the same reference signs, and description thereof will be omitted as appropriate.

In the portion indicated by an arrow W41 in FIG. 10, an illumination intensity distribution at the surgical site is depicted when the surgical site is illuminated by each of the indwelling light sources 25 at the normal illumination intensity. Also, in the portion indicated by an arrow W42 in FIG. 10, an illumination intensity distribution at the surgical site is depicted when the surgical site is illuminated by each of the indwelling light sources 25 at the low illumination intensity.

Further, in the portions indicated by the arrows W41 and W42, each of the concentric circles depicts the manner in which the surgical site is illuminated by one of the indwelling light sources 25. The shading of each region represents illumination intensity produced by illuminating light.

In the example illustrated in FIG. 10, uneven illumination is present, and the portion indicated by the arrow W41 has uneven illumination intensity distribution, i.e., uneven luminance distribution. For example, the illumination intensity is high at the position of the observation point "a" indicated by the arrow Q31 and that of the observation point "b" indicated by the arrow Q32. However, the illumination intensity is lower at the position of the observation point "c" indicated by the arrow Q33 than those of the observation points "a" and "b."

Similarly, uneven illumination is somewhat present in the portion indicated by the arrow W42, thus resulting in a rather non-uniform overall illumination intensity distribution, i.e., luminance distribution.

However, the portion indicated by the arrow W42 has significantly lower uneven illumination than in a case where the portion is illuminated at the normal illumination intensity although dark as a whole due to illumination at the low illumination intensity. In other words, the illumination intensity distribution is approximately uniform.

In this example, uneven illumination is present. Therefore, the rate of increase in luminance value (pixel value) at the same position (pixel) of a frame of the endoscopic image under illumination at the normal illumination intensity relative to the frame of the endoscopic image under illumination at the low illumination intensity varies from one position to another in the frame of the endoscopic image, i.e., varies depending on the position of the observation point.

That is, for example, $(I_a'-I_a)/I_a$ $(I_b'-I_b)/I_b$ holds for the observation points "a" and "b," and the luminance values $I_a'$ and $I_b'$ are not equal $(I_a' I_b')$ even when the luminance values $I_a$ and $I_b$ are equal $(I_a=I_b)$. The difference between the luminance values $I_a'$ and $I_b'$ at this time is uneven illumination.

As described above, the signal processing section 53 calculates an uneven illumination correction parameter at each pixel position, i.e., at each observation point, on the basis of a normally illuminated frame and a low illuminated frame adjacent to each other in time.

If an uneven illumination correction parameter is calculated by using two frames adjacent to each other, the time interval between the two frames used for the calculation is the shortest. As a result, it is possible to minimize impact attributable to luminance variation factors other than uneven illumination such as movement of the subject caused by blood flow and pulsation of the surgical site.

During calculation of the uneven illumination correction parameter, each pixel position in the frame (endoscopic image) is used as an observation point, and a predetermined given observation point such as the center position of the frame is used as a reference observation point. Also, of the observation points in the frame, the observation point to which attention is directed will be also referred to as an observation point of interest.

A description will be given below assuming, as a specific example, that the observation point "a" described above is used as a reference observation point (hereinafter also referred to as the reference observation point "a") and the observation point "b" is used as an observation point of interest (hereinafter also referred to as the reference observation point "b"). It should be noted that, in a normally illuminated frame and a low illuminated frame used to calculate the uneven illumination correction parameter, the position of the reference observation point "a" in the normally illuminated frame and the position of the reference observation point "a" in the low illuminated frame have the same positional relationship. Similarly, the position of the observation point of interest "b" in the normally illuminated frame and the position of the observation point of interest "b" in the low illuminated frame have the same positional relationship.

In a case where the uneven illumination correction parameter is calculated for the observation point of interest "b," the rate of change in luminance $(I_b'-I_b)/I_b$ at the observation point of interest "b" is normalized with the rate of change in luminance $(I_a'-I_a)/I_a$ at the reference observation point "a" first to find a normalized rate of change in luminance $r_{b,a}$, a ratio of the rate of change in luminance at the observation point of interest "b" relative to that at the reference observation point "a." That is, the normalized rate of change in luminance $r_{b,a}$ is calculated by using the following formula (1):

[Math. 1]

$$r_{b,a}\{(I_b'-I_b)/I_b\}/\{(I_a'-I_a)/I_a\} \qquad (1)$$

Next, a reciprocal of the acquired normalized rate of change in luminance $r_{b,a}$ is found, and the acquired reciprocal is used as an uneven illumination correction parameter $h_{b,a}$ of the observation point of interest "b." That is, the uneven illumination correction parameter $h_{b,a}$ is calculated by using the following formula (2):

[Math. 2]

$$h_{b,a} = 1/r_{b,a} = \frac{I_a'-I_a}{I_b'-I_b} \times \frac{I_b}{I_a} \qquad (2)$$

The uneven illumination correction parameter $h_{b,a}$ acquired as described above makes it possible to correct the rate of change in luminance at the observation point of interest "b" in a manner similar to the rate of change in luminance at the reference observation point "a."

During the uneven illumination correction process, the luminance value (pixel value) at the observation point of interest "b" in each frame of the endoscopic image is corrected by using the uneven illumination correction parameter $h_{b,a}$.

For example, when the luminance value $I_b'$ at the observation point of interest 'b' in the normally illuminated frame described above is corrected by the uneven illumination correction process using the uneven illumination correction parameter $h_{b,a}$, a corrected luminance value $I_{hb}'$ is calculated by using the following formula (3):

[Math. 3]

$$I'_{hb}=h_{b,a}\times(I'_b-I_b)+b \qquad (3)$$

Also, for example, an uneven illumination correction parameter $h_{a,a}$ of the reference observation point "a" is the reciprocal of a normalized rate of change in luminance $r_{a,a}$ of the reference observation point "a" acquired by a calculation similar to the above formula (1). Therefore, the uneven illumination correction parameter $h_{a,a}$ can be found by using the following formula (4), and this parameter is 1.

[Math. 4]

$$h_{a,a}=1/r_{a,a}=1 \qquad (4)$$

Therefore, if, for example, the luminance value $I_a'$ of the normally illuminated frame at the reference observation point "a" is corrected by the uneven illumination correction process, the calculation in the following formula (5) is carried out, thus calculating a corrected luminance value $I_{ha}'$.

[Math. 5]

$$I'_{ha}=h_{a,a}\times(I'_a-I_a)+I_a=(I'_a-I_a)+I_a=I'_a \qquad (5)$$

It is clear from the calculation in formula (5) that the luminance value at the reference observation point "a" remains unchanged between before and after the correction.

Further, we assume, for example, that the reference observation point "a" and the observation point of interest "b" have the same luminance value in the low illuminated frame. That is, we assume that the luminance values $I_a$ and $I_b$ are equal ($I_a = I_b$).

In this case, the uneven illumination correction parameter $h_{b,a}$ at the observation point of interest "b" is given as illustrated in the following formula (6):

[Math. 6]

$$h_{b,a} = \frac{I'_a - I_a}{I'_b - I_b} \times \frac{I_b}{I_a} = \frac{I'_a - I_a}{I'_b - I_b} \times \frac{I_a}{I_a} = \frac{I'_a - I_a}{I'_b - I_b} \tag{6}$$

Therefore, when the luminance value $I_b'$ of the normally illuminated frame at the observation point of interest "b" is corrected by the uneven illumination correction process using the uneven illumination correction parameter $h_{b,a}$ acquired by the calculation in the formula (6), the luminance value $I_{hb}'$ illustrated in the following formula (7) is acquired. That is, the calculation in the following formula (7) is carried out in the uneven illumination correction process, thus calculating the corrected luminance value $I_{hb}'$.

[Math. 7]

$$I'_{hb} = h_{b,a} \times (I'_b - I_b) + I_b = \frac{I'_a - I_a}{I'_b - I_b} \times (I'_b - I_b) + I_a = I'_a = I'_{ha} \tag{7}$$

As is clear from the calculation result of the Math (7), the corrected luminance value $I_{hb}'$ is equal to the corrected luminance value $I_{ha}'$ of the normally illuminated frame at the reference observation point "a." In the normally illuminated frame after the uneven illumination correction process, therefore, the luminance values are equal at the reference observation point "a" and the observation point of interest "b," thus making it clear that the uneven illumination has been corrected properly.

The uneven illumination correction process as described above permits correction of the luminance value at each observation point in such a manner as to ensure that the illumination intensity distribution, i.e., the luminance distribution in each frame of the endoscopic image, is approximately the same as the luminance distribution of the low illuminated frame, a frame with minimal uneven illumination.

This allows for proper correction of uneven illumination.

<Description of Parameter Calculation Process>

A description will be given next of the processes performed by the endoscopic system 11 described above.

Figure 11:
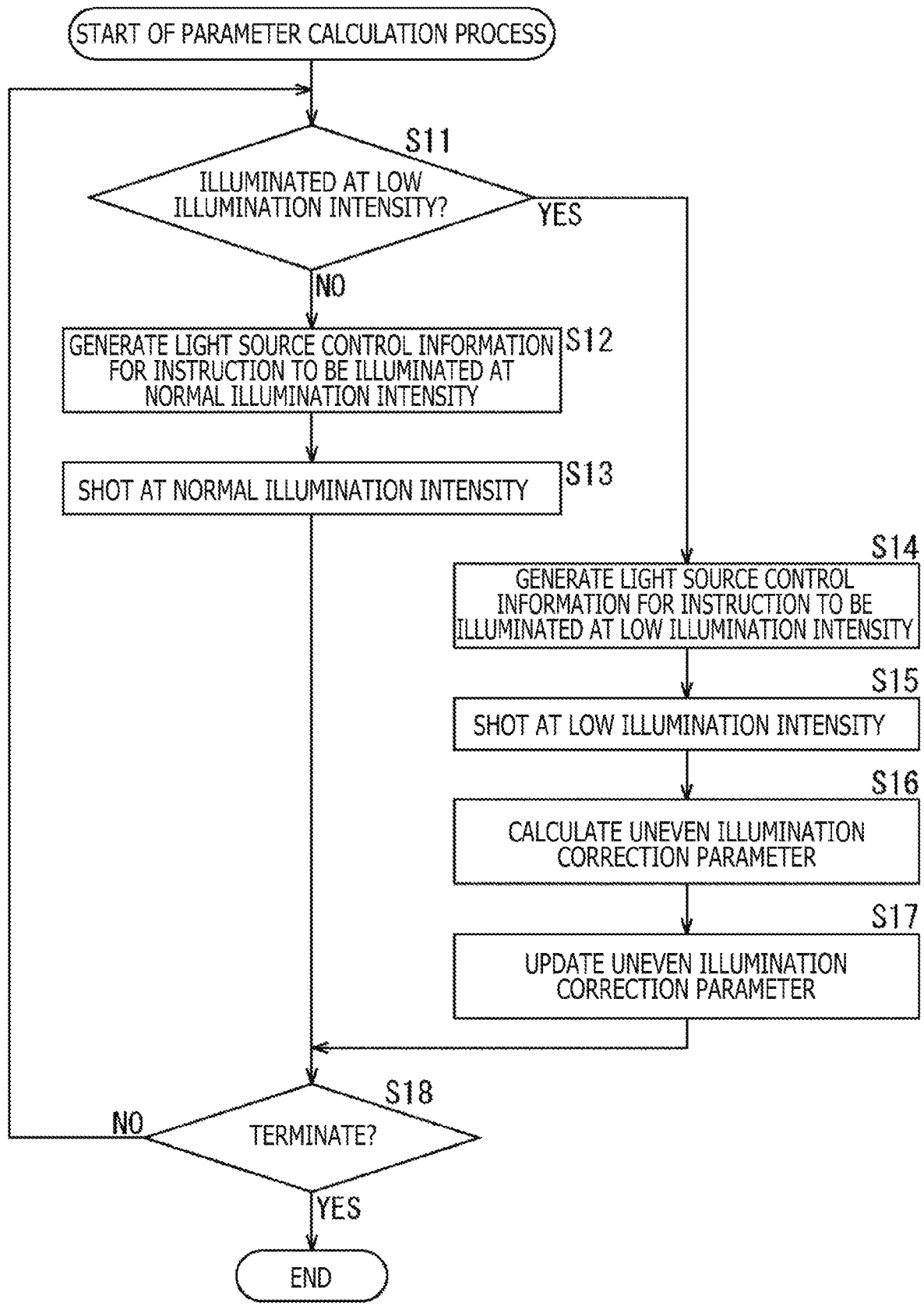
FIG. 11 is a flowchart describing a parameter calculation process.

A description will be given first of the parameter calculation process with reference to a flowchart of FIG. 11, a process for calculating an uneven illumination correction parameter, performed by the endoscopic system 11 together with the shooting of an endoscopic image.

In step S11, the light source control section 51 determines whether or not to perform illumination at the low illumination intensity.

For example, the endoscopic system 11 basically illuminates the surgical site at the normal illumination intensity but performs illumination at the low illumination intensity only for a one-frame-long shooting time period of the endoscopic image at a constant time interval. In this case, when time comes to perform illumination at the low illumination intensity, a determination is made in step S11 to proceed with illumination at the low illumination intensity.

In a case where a determination is made in step S11 not to perform illumination at the low illumination intensity, i.e., to perform illumination at the normal illumination intensity, the light source control section 51 generates, in step S12, light source control information for instructing that illumination be performed at the normal illumination intensity.

Then, the light source control section 51 supplies the generated light source control information to the control signal source 24 and the signal processing section 53. Also, the control signal source 24 generates a light source control signal on the basis of the light source control information supplied from the light source control section 51, and the transmission section 61 of the control signal source 24 sends the light source control signal through wireless communication. As a result, the reception sections 71 of the indwelling light sources 25 receive the light source control signal sent from the control signal source 24.

In step S13, the endoscopic system 11 shoots the surgical site at the normal illumination intensity.

That is, the indwelling light sources 25 shine (output) illuminating light onto (to) the surgical site at the normal illumination intensity on the basis of the light source control signal received from the control signal source 24 as a result of the process in step S12.

When illuminating light is shined onto the surgical site as described above, the illuminating light is reflected by the surgical site and enters the rigid endoscopic scope 31. As a result, the reflected light that has entered the rigid endoscopic scope 31 is guided by the observation optics inside the rigid endoscopic scope 31, thus entering the image sensor 41.

The image sensor 41 receives the reflected light that has entered the image sensor 41 from the surgical site via the rigid endoscopic scope 31 and converts the reflected light into an electric signal, thus shooting the surgical site. Also, the image sensor 41 supplies a frame worth of image data of the endoscopic image acquired by the shooting to the signal processing section 53.

At this time, image data supplied to the signal processing section 53 is image data of the normally illuminated frame of the endoscopic image. The signal processing section 53 can find out, from the light source control information supplied from the light source control section 51, whether illumination is performed at the normal illumination intensity or at the low illumination intensity. This makes it possible to carry out signal processing on the image data acquired from the shooting in synchronism with illumination control.

When a normally illuminated frame is acquired as a result of the shooting with the surgical site illuminated at the normal illumination intensity as described above, and the process proceeds thereafter to step S18.

On the other hand, in a case where a determination is made in step S11 to proceed with illumination at the low illumination intensity, the light source control section 51 generates, in step S14, light source control information for instructing that illumination be performed at the low illumination intensity and supplies the light source control information to the control signal source 24 and the signal processing section 53.

Also, the control signal source 24 generates a light source control signal on the basis of the light source control information supplied from the light source control section 51, and the transmission section 61 of the control signal source 24 sends the light source control signal through wireless communication. As a result, the reception sections 71 of the indwelling light sources 25 receive the light source control signal sent from the control signal source 24.

In step S15, the endoscopic system 11 shoots the surgical site at the low illumination intensity.

That is, the indwelling light sources 25 shine (output) illuminating light onto (to) the surgical site at the low illumination intensity on the basis of the light source control signal received from the control signal source 24 as a result of the process in step S14.

When illuminating light is shined onto the surgical site as described above, the illuminating light is reflected by the surgical site and enters the rigid endoscopic scope 31 as in the case of step S13. As a result, the reflected light enters the image sensor 41 via the rigid endoscopic scope 31.

The image sensor 41 receives the reflected light that has entered the image sensor 41 from the surgical site via the rigid endoscopic scope 31 and converts the reflected light into an electric signal, thus shooting the surgical site and supplying a frame worth of image data of the endoscopic image acquired by the shooting to the signal processing section 53. At this time, image data supplied to the signal processing section 53 is image data of a normally illuminated frame of the endoscopic image.

When a low illuminated frame is acquired as a result of the shooting with the surgical site illuminated at the low illumination intensity as described above, the process proceeds to step S16.

In step S16, the signal processing section 53 calculates an uneven illumination correction parameter on the basis of image data of a low illuminated frame acquired by the process in step S15 and image data of a normally illuminated frame, the frame immediately previous in time to the low illuminated frame.

For example, the signal processing section 53 carries out the same calculations as the formulas (1) and (2) described above and calculates an uneven illumination correction parameter for each observation point (pixel) of the endoscopic image. In this case, an uneven illumination correction parameter is calculated for each pixel by using the luminance values of the pixels having the same positional relationship in the low illuminated frame and the normally illuminated frame.

In step S17, the signal processing section 53 updates the uneven illumination correction parameter. That is, the signal processing section 53 supplies the uneven illumination correction parameter acquired by the process in step S16 to the uneven illumination correction parameter recording section 52, thus causing the uneven illumination correction parameter recorded in the uneven illumination correction parameter recording section 52 to be rewritten (overwritten) by the newly supplied uneven illumination correction parameter.

When the uneven illumination correction parameter is updated as described above, the process proceeds thereafter to step S18.

When the process in step S13 or the process in step S17 is performed, the signal processing section 53 determines in step S18 whether or not to terminate the process. For example, in a case where the shooting of the endoscopic image ends, a determination is made in step S18 to terminate the process.

In a case where a determination is made in step S18 not to terminate the process, the process returns to step S11, and the processes described above are repeated. That is, a next frame of the endoscopic image is shot, and the uneven illumination correction parameter is updated as appropriate.

In contrast, in a case where a determination is made in step S18 to terminate the process, the parameter calculation process ends.

As described above, the endoscopic system 11 shoots an endoscopic image while controlling the illumination intensity and updates the uneven illumination correction parameter when a low illuminated frame is shot. It is possible to correct uneven illumination of the endoscopic image properly by using an uneven illumination correction parameter calculated as described above. That is, the uneven illumination distribution can be reduced.

<Description of Output Image Generation Process>

Figure 12:
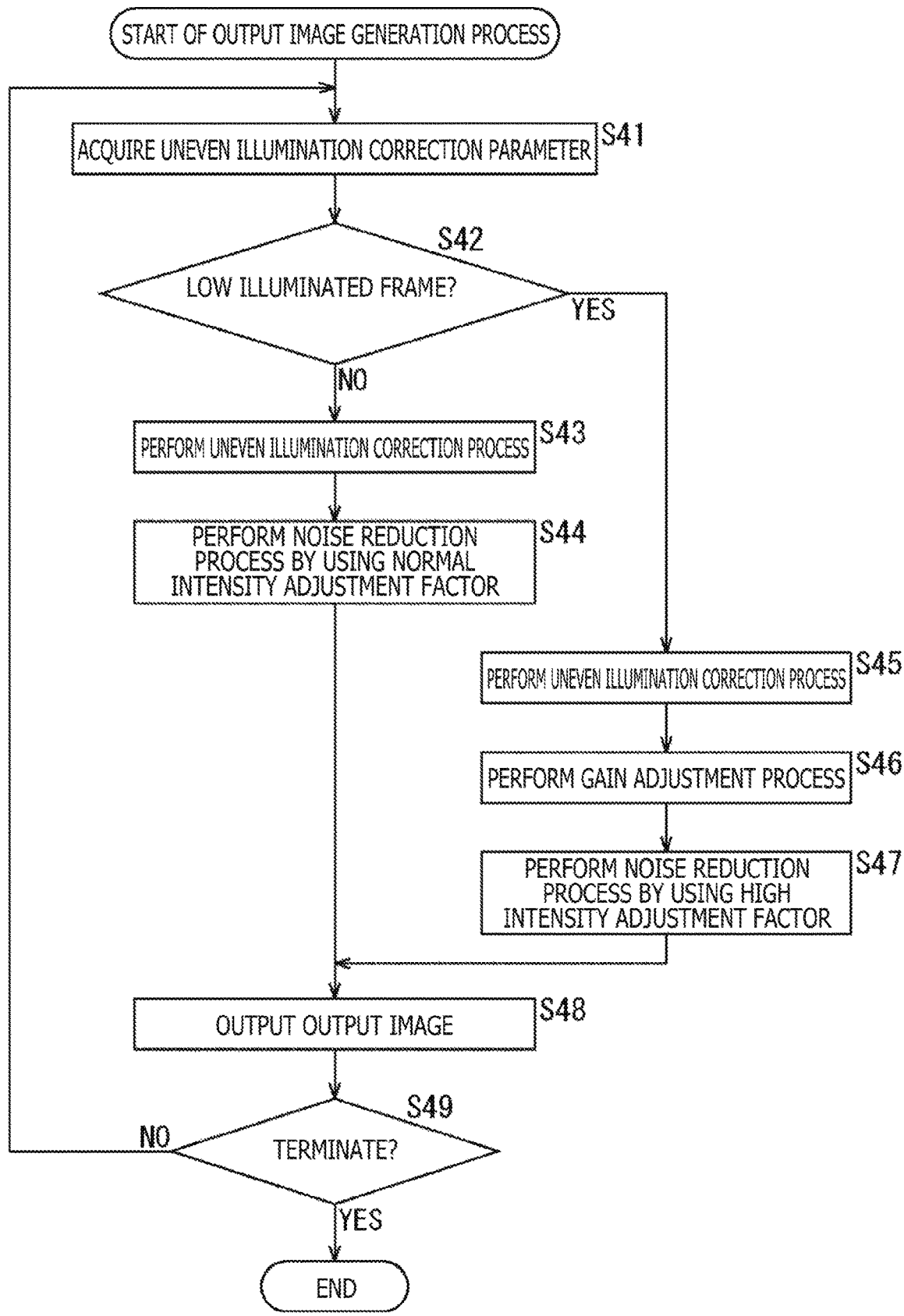
FIG. 12 is a flowchart describing an output image generation process.

A description will be given next of an output image generation process performed in parallel with the parameter calculation process described with reference to FIG. 11. That is, a description will be given below of the output image generation process performed by the endoscopic system 11 with reference to the flowchart illustrated in FIG. 12.

In step S41, when a frame worth of image data of the endoscopic image is supplied from the image sensor 41, the signal processing section 53 acquires the uneven illumination correction parameter recorded in the uneven illumination correction parameter recording section 52. That is, the uneven illumination correction parameter is read out.

In step S42, the signal processing section 53 determines whether the frame supplied from the image sensor 41 is a low illuminated frame shot under illumination at the low illumination intensity.

In a case where it is determined in step S42 that the supplied frame is not a low illuminated frame, i.e., a normally illuminated frame, the process proceeds to step S43.

In step S43, the signal processing section 53 performs the uneven illumination correction process on the normally illuminated frame supplied from the image sensor 41 on the basis of the uneven illumination correction parameter acquired in step S41. For example, the signal processing section 53 corrects the luminance value of each pixel by performing a similar calculation to the formula (3) described above for each pixel (observation point) of the normally illuminated frame, thus reducing uneven illumination.

In step S44, the signal processing section 53 performs the noise reduction process on the normally illuminated frame acquired by the process in step S43 that has been subjected to the uneven illumination correction process by using the normal intensity adjustment factor. That is, the signal processing section 53 multiplies the NR filtering factor by the normal intensity adjustment factor made available in advance and performs, as the noise reduction process, the filtering process on the normally illuminated frame by using the factor acquired as a result of the multiplication. Then, the signal processing section 53 uses the frame acquired by the noise reduction process as a frame of the output image.

When an output image frame is acquired, the process proceeds thereafter to step S48.

In contrast, in a case where it is determined in step S42 that the supplied frame is a low illuminated frame, the process proceeds to step S45.

In step S45, the signal processing section 53 performs the uneven illumination correction process on the low illuminated frame supplied from the image sensor 41 on the basis of the uneven illumination correction parameter acquired in step S41.

For example, the signal processing section 53 corrects the luminance value of each pixel by performing a similar calculation to the Math (3) described above for each pixel (observation point) of the low illuminated frame, thus reducing uneven illumination.

In step S46, the signal processing section 53 performs the gain adjustment process on the low illuminated frame acquired by the process in step S45 that has been subjected to the uneven illumination correction process.

During the gain adjustment process, a gain value is used that has been calculated, for example, from the normally illuminated frame, the low illuminated frame, and so on as described above.

In step S47, the signal processing section 53 performs, by using the high intensity adjustment factor, the noise reduction process on the low illuminated frame acquired by the process in step S46 that has been subjected to the gain adjustment process.

That is, the signal processing section 53 multiplies the NR filtering factor by the high intensity adjustment factor made available in advance and performs, as the noise reduction process, the filtering process on the low illuminated frame by using the factor acquired as a result of the multiplication. Then, the signal processing section 53 uses the frame acquired by the noise reduction process as a frame of the output image.

When an output image frame is acquired, the process proceeds thereafter to step S48.

When an output image frame is acquired following the process in step S44 or the process in step S47, the signal processing section 53 outputs, in step S48, the acquired output image frame to the monitor 22 for display.

In step S49, the signal processing section 53 determines whether or not to terminate the process. For example, in a case where the display of the output image ends, a determination is made in step S49 to terminate the process.

In a case where a determination is made in step S49 not to terminate the process, the process returns to step S41, and the processes described above are repeated. That is, a next frame of the output image is generated and output.

In contrast, in a case where a determination is made in step S49 to terminate the process, the output image generation process ends.

As described above, the endoscopic system 11 performs the uneven illumination correction process and other processes on frames of an endoscopic image acquired by shooting, thus generating an output image. The uneven illumination correction process and other processes provide an output image whose uneven illumination has been corrected. That is, the uneven illumination distribution can be reduced.

<Configuration Example of Computer>

Incidentally, the series of processes described above can be performed by hardware or software. In a case where the series of processes are performed by software, the program included in the software is installed to a computer. Here, the computer includes a computer incorporated in dedicated hardware, a general-purpose computer capable of performing a variety of functions as a result of installation of various programs, and so on.

FIG. 13 is a block diagram illustrating a hardware configuration example of a computer for performing the above series of processes using a program.

In a computer, a CPU (Central Processing Unit) 501, a ROM (Read Only Memory) 502, and a RAM (Random Access Memory) 503 are connected to each other by a bus 504.

An I/O interface 505 is further connected to the bus 504. An input section 506, an output section 507, a recording section 508, a communication section 509, and a drive 510 are connected to the I/O interface 505.

The input section 506 includes a keyboard, a mouse, a microphone, an imaging element, and so on. The output section 507 includes a display, a speaker, and so on. The recording section 508 includes a hard disk, a non-volatile memory, and so on. The communication section 509 includes a network interface and so on. The drive 510 drives a removable recording medium 511 such as magnetic disk, optical disc, magneto-optical disk, or semiconductor memory.

In the computer configured as described above, the CPU 501 loads, for example, the program recorded in the recording section 508 into the RAM 503 via the I/O interface 505 and the bus 504 for execution, thereby allowing the above series of processes to be performed.

The program executed by the computer (CPU 501) can be recorded, for example, in the removable recording medium 511 as a packaged media or the like, and provided. Also, the program can be provided via a wired or wireless transport media such as local area network, the Internet, and digital satellite broadcasting.

In the computer, the program can be installed to the recording section 508 via the I/O interface 505 by inserting the removable recording medium 511 into the drive 510. Also, the program can be received by the communication section 509 via a wired or wireless transport media and installed to the recording section 508. In addition to the above, the program can be installed in advance to the ROM 502 or the recording section 508.

It should be noted that the program executed by the computer may perform the processes chronologically in accordance with the sequence described in the present specification, or in parallel, or at a necessary time as when the program is called.

It should be noted that embodiments of the present technology are not limited to those described above and can be modified in various ways without departing from the gist of the present technology.

For example, the present technology can have a cloud computing configuration in which one function is processed by a plurality of apparatuses via a network in a shared and cooperative manner.

Also, each of the steps described in the above flowcharts can be performed not only by a single apparatus but also by a plurality of apparatuses in a shared manner.

Further, in a case where one step includes a plurality of processes, the plurality of processes included in that step can be performed not only by a single apparatus but also by a plurality of apparatuses in a shared manner.

Also, the effects described in the present specification are merely illustrative and are not restrictive and that there may be other effects.

Further, the present technology can have the following configurations:

(1)

An image processing apparatus including:

a signal processing section adapted to correct uneven illumination of an image shot with a subject within a body of a patient to be operated on illuminated by a light source, the light source being arranged within the patient's body, the signal processing section correcting uneven illumination on the basis of a normally illuminated image shot with the subject within the body illuminated at a given illumination intensity and a low illuminated image shot with the subject illuminated at a lower illumination intensity than the given illumination intensity.

(2)
The image processing apparatus according to (1), in which the low illuminated image includes an image shot with illumination produced by the light source halted.
(3)
The image processing apparatus according to (1) or (2) further including:
a light source control section adapted to control illumination produced by the light source.
(4)
The image processing according to any one of (1) to (3), in which
the signal processing section calculates a correction parameter for correcting the uneven illumination on the basis of the normally illuminated image and the low illuminated image and corrects the uneven illumination of the image on the basis of the correction parameter.
(5)
The image processing apparatus according to (4), in which the signal processing section calculates the correction parameter on the basis of a rate of change in luminance between the normally illuminated image and the low illuminated image.
(6)
The image processing apparatus according to (5), in which the signal processing section calculates the correction parameter at a given position on the basis of the rate of change in luminance at the given position and the rate of change in luminance at a position different from the given position.
(7)
The image processing apparatus according to any one of (1) to (6) further including:
a shooting section including a rigid endoscopic scope and adapted to shoot the image by receiving light incident from the subject within the body via the rigid endoscopic scope.
(8)
The image processing apparatus according to any one of (1) to (7), in which
the image includes a video including each of the normally illuminated image and the low illuminated image as a frame.
(9)
The image processing apparatus according to (8), in which
the signal processing section generates an output video by correcting the uneven illumination of a video and performing a noise reduction process on the video acquired by the uneven illumination correction.
(10)
The image processing apparatus according to (9), in which
in a case where the video frame includes the low illuminated image, the signal processing section generates a frame of the output video by correcting the uneven illumination of the low illuminated image first, followed by adjusting a gain and performing the noise reduction process on the image acquired by the gain adjustment, and
in a case where the video frame includes the normally illuminated image, the signal processing section generates a frame of the output video by correcting the uneven illumination of the normally illuminated image and performing the noise reduction process on the image acquired by the uneven illumination correction.
(11)
The image processing apparatus according to (10), in which in a case where the video frame includes the low illuminated image, the signal processing section performs the noise reduction process on the image acquired by the gain adjustment at a higher processing intensity than in a case where the video frame includes the normally illuminated image.
(12)
An image processing method including:
a step of correcting uneven illumination of an image shot with a subject within a body of a patient to be operated on illuminated by a light source, the light source being arranged within the patient's body, the uneven illumination being corrected on the basis of a normally illuminated image shot with the subject within the body illuminated at a given illumination intensity and a low illuminated image shot with the subject illuminated at a lower illumination intensity than the given illumination intensity.
(13)
An endoscopic system including:
a shooting section including a rigid endoscopic scope and adapted to shoot an image by receiving light incident from a subject within a body of a patient to be operated on via the rigid endoscopic scope; and
a signal processing section adapted to correct uneven illumination of the image shot by the shooting section with the subject within the patient's body illuminated by a light source arranged within the patient's body on the basis of a normally illuminated image shot with the subject within the body illuminated at a given illumination intensity and a low illuminated image shot with the subject illuminated at a lower illumination intensity than the given illumination intensity.

REFERENCE SIGNS LIST

11 Endoscopic system, 21 Shooting section, 23 CCU, 24 Control signal source, 25-1 to 25-N, 25 Indwelling light sources, 31 Rigid endoscopic scope, 32 Camera head, 41 Image sensor, 51 Light source control section, 52 Uneven illumination correction parameter recording section, 53 Signal processing section

The invention claimed is:
1. An image processing apparatus, comprising:
a processor configured to:
correct uneven illumination of an image of a subject within a body of a patient based on a normally illuminated image shot with the subject illuminated at a first illumination intensity and a low illuminated image shot with the subject illuminated at a second illumination intensity, wherein
the subject is illuminated by a light source arranged within the body of the patient,
the second illumination intensity is lower than the first illumination intensity, and
the image includes a video that includes each of the normally illuminated image and the low illuminated image as a frame;
in a case where the frame includes the low illuminated image, generate a first frame of output video by first correction of the uneven illumination of the low illuminated image, gain adjustment on the first frame of the output video, and execution of a noise reduction process on a first image acquired by the gain adjustment; and
in a case where the frame includes the normally illuminated image, generate a second frame of the output video by second correction of the uneven illumination of the normally illuminated image and execution of the noise reduction process on a second image acquired by the second correction.

2. The image processing apparatus according to claim 1, wherein the low illuminated image is captured with illumination produced by the light source halted.

3. The image processing apparatus according to claim 1, wherein the processor is further configured to control illumination produced by the light source.

4. The image processing apparatus according to claim 1, wherein the processor is further configured to:
   calculate a correction parameter for correction of the uneven illumination based on the normally illuminated image and the low illuminated image; and
   correct the uneven illumination of the image based on the correction parameter.

5. The image processing apparatus according to claim 4, wherein the processor is further configured to calculate the correction parameter based on a rate of change in luminance between the normally illuminated image and the low illuminated image.

6. The image processing apparatus according to claim 5, wherein the processor is further configured to calculate the correction parameter at a specific position based on the rate of change in luminance at the specific position and the rate of change in luminance at a position different from the specific position.

7. The image processing apparatus according to claim 1, further comprising:
   a shooting section including a rigid endoscopic scope, wherein the shooting section is configured to shoot the image based on reception of light incident from the subject within the body via the rigid endoscopic scope.

8. The image processing apparatus according to claim 1, wherein in the case where the video frame includes the low illuminated image, the processor is further configured to execute the noise reduction process on the first image acquired by the gain adjustment at a higher processing intensity than in the case where the frame includes the normally illuminated image.

9. An image processing method, comprising:
   correcting uneven illumination of an image of a subject within a body of a patient based on a normally illuminated image shot with the subject illuminated at a first illumination intensity and a low illuminated image shot with the subject illuminated at a second illumination intensity, wherein
      the subject is illuminated by a light source arranged within the body of the patient,
      the second illumination intensity is lower than the first illumination intensity, and
      the image includes a video that includes each of the normally illuminated image and the low illuminated image as a frame;
   in a case where the frame includes the low illuminated image, generating a first frame of output video by first correction of the uneven illumination of the low illuminated image, gain adjustment on the first frame of the output video, and execution of a noise reduction process on a first image acquired by the gain adjustment; and
   in a case where the frame includes the normally illuminated image, generating a second frame of the output video by second correction of the uneven illumination of the normally illuminated image and execution of the noise reduction process on a second image acquired by the second correction.

10. An endoscopic system, comprising:
a shooting section that includes a rigid endoscopic scope, wherein the shooting section is configured to shoot an image by reception of light incident from a subject within a body of a patient via the rigid endoscopic scope; and
a processor configured to:
   correct uneven illumination of the image of the subject within the body of the patient based on a normally illuminated image shot with the subject illuminated at a first illumination intensity and a low illuminated image shot with the subject illuminated at a second illumination intensity, wherein
      the subject is illuminated by a light source arranged within the body of the patient,
      the second illumination intensity is lower than the first illumination intensity, and
      the image includes a video that includes each of the normally illuminated image and the low illuminated image as a frame;
   in a case where the frame includes the low illuminated image, generate a first frame of output video by first correction of the uneven illumination of the low illuminated image, gain adjustment on the first frame of the output video, and execution of a noise reduction process on a first image acquired by the gain adjustment; and
   in a case where the frame includes the normally illuminated image, generate a second frame of the output video by second correction of the uneven illumination of the normally illuminated image and execution of the noise reduction process on a second image acquired by the second correction.

* * * * *